(12) United States Patent
Seki et al.

(10) Patent No.: US 8,522,628 B2
(45) Date of Patent: Sep. 3, 2013

(54) LIQUID SAMPLE ANALYZING APPARATUS AND LIQUID SAMPLE INTRODUCING APPARATUS

(75) Inventors: Yoshiaki Seki, Hitachinaka (JP);
Kimihiko Ishii, Hitachinaka (JP);
Mitsuhiko Ueda, Hitachinaka (JP);
Katsutoshi Shimizu, Hitachinaka (JP);
Hiroshi Suzuki, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/503,694

(22) PCT Filed: Oct. 20, 2010

(86) PCT No.: PCT/JP2010/068467
§ 371 (c)(1),
(2), (4) Date: Apr. 24, 2012

(87) PCT Pub. No.: WO2011/052445
PCT Pub. Date: May 5, 2011

(65) Prior Publication Data
US 2012/0216632 A1 Aug. 30, 2012

(30) Foreign Application Priority Data
Oct. 26, 2009 (JP) .................................. 2009-245414

(51) Int. Cl.
*G01N 35/10* (2006.01)
(52) U.S. Cl.
USPC ..................................................... 73/864.21
(58) Field of Classification Search
None
See application file for complete search history.

(56) References Cited

U.S. PATENT DOCUMENTS

| | | | | |
|---|---|---|---|---|
| 4,836,038 A | * | 6/1989 | Baldwyn | .................... 73/864.21 |
| 6,066,298 A | * | 5/2000 | Fukunaga | ..................... 422/510 |
| 2008/0134804 A1 | | 6/2008 | Maeda et al. | |
| 2010/0326215 A1 | * | 12/2010 | Maeda et al. | .............. 73/864.21 |
| 2011/0120213 A1 | * | 5/2011 | Hirayama et al. | ........... 73/61.55 |

FOREIGN PATENT DOCUMENTS

| | | |
|---|---|---|
| CN | 101196497 | 6/2008 |
| JP | 01-248055 A | 10/1989 |
| JP | 06-235722 A | 8/1994 |
| JP | 2006-292641 A | 10/2006 |
| JP | 2008-145112 A | 6/2008 |

OTHER PUBLICATIONS

International Preliminary Report on Patentability and Written Opinion in PCT/JP2010/068467, dated May 18, 2012.

* cited by examiner

*Primary Examiner* — Robert R Raevis
(74) *Attorney, Agent, or Firm* — Mattingly & Malur, PC

(57) ABSTRACT

A liquid sample introducing apparatus capable of executing a process with high reliability and high speed is realized. An injection valve includes a sample storage loop connected to a mobile phase flow passage for supplying a sample to a detector of a liquid chromatograph apparatus. A sample is sucked in a needle through a valve and a pipe by a syringe, being introduced to the sample storage loop, being supplied to the mobile phase flow passage. A washing solution from a washing solution bottle is supplied to the needle by a washing unit through the valve and the pipe to wash the inner wall of the needle. The washing solution from the washing solution bottle is supplied to a washing tank by the washing unit through the valve and a pipe to wash the external wall of the needle in the washing tank.

7 Claims, 43 Drawing Sheets

LIQUID SAMPLE ANALYZING APPARATUS AND LIQUID SAMPLE INTRODUCING APPARATUS

TECHNICAL FIELD

This invention relates to a liquid sample analyzing apparatus and liquid sample introducing apparatus.

BACKGROUND ART

In a liquid chromatograph apparatus of one kind of a liquid sample analyzing apparatus, a mobile phase is sucked into the apparatus by a pump unit, being fed to a separation column with a sample introduced by an automatic sample introduction unit. The sample introduced in the separation column is separated into components to be detected by various kinds of detectors. Generally, in a field of an apparatus so called a high performance liquid chromatography (HPLC), an analysis operation is required to be operated under high pressure flow passage at 20 to 40 M Pa at its maximum. In a pump unit used for HPLC as described above, it is required that a mobile phase can be supplied to the apparatus correctly and precisely even under high pressure condition.

Further, the automatic sample introducing unit is used as an apparatus which sucks the sample liquid by using a needle from a sample holding container lined up on sample rack, thereafter, the apparatus stores the sample in a sample storage loop to discharge the sample into a mobile phase flow passage of the liquid chromatography automatically. Furthermore, there are automatic sample introduction units having a pre-processing function for diluting a sample before discharging into mobile phase flow passage and for mixing the sample and reaction reagent for labeling, or the like.

The injection system in the above automatic sample introduction apparatus is generally divided into two kinds. In one kind of an injection system which is a direct injection system (refer to the patent document 1 and the patent document 2), a needle and a sample storage loop are integrated into a mobile phase flow passage under high pressure condition. In the other kind of an injection system which is a loop injection system (refer to the patent document 3), only a needle is integrated into a mobile phase flow passage under high pressure condition.

In the direct injection system, a sample temporarily stored in the needle and the sample storage loop is pushed out toward the column by the mobile phase at the start of analysis, and the mobile phase is always flushed in the needle and the sample storage loop during the analysis operation, so that the sucked sample can be introduced into the column without waste of the sample, and the is no need for installing other unit for washing the inner of the needle contaminated by the sample. It is the merit of the direct injection system.

On one hand, since the needle is integrated into one part of the mobile phase flow passage in principle, a construction is required for keeping the fluid-tight between the needle and the sample injection port under the high pressure condition. Accordingly, the direct injection system is not suitable for handling of diluting and mixing the sample in the pre-process. It is the demerit of the direct injection system.

On the other hand, according to the loop injection system, since the needle is positioned outside of the mobile phase flow passage under high pressure condition during the analysis operation, the movement of the needle and the sample accounting operation can be executed during the analysis operation. Accordingly, a construction is not required for keeping the high pressure between the needle and the sample injection port, so that the pre-process of the sample can be executed during the analysis operation. It is the merit of the loop injection system. However, the loop injection system requires an equipment and process for washing the inner of the needle, so that the loop injection system may require long time for injecting a sample in comparison with the direct injection system. It is the demerit of the loop injection system.

Recently, so called an ultra high performance liquid chromatography (UHPLC) is rapidly advanced by the advance of the column bulking agent refine technologies. In the UHPLC, an analysis operation is executed under 60 to 120 M Pa at its maximum, the analysis time per one sample is several ten seconds to several minutes which are one per several times of the conventional HPLC, so that the through put of an analysis operation can be improved remarkably.

The basic item of an automatic sample introducing unit required for the UHPLC is to have high injection quantity repeatability, low carry over, high speed process (reducing of cycle time), high reliability, and high durability against multiple samples analysis request under ultra high pressure of 60 to 120 M Pa at its maximum.

In general, a sample introduction apparatus employing the direct injection system has a mechanism which can always keep the fluid-tight between the needle and the seal in the sample injection port in order to avoid the ejection of the mobile phase form the sample inlet port even under high pressure condition. During the analysis operation, the needle integrated in the high pressure flow passage and the sample storage loop are separated from the high pressure flow passage by the flow passage exchange valve at the sample suction step, the needle and the solvent in the sample storage loop being exposed under the atmospheric pressure.

Further, after the needle and the solvent are exposed under the atmospheric pressure, the needle is inserted into the sample hold container, and the sample is sucked into the needle or sample storage loop, thereafter, the needle is moved at the above-mentioned sample injection port. At this step, the flow passage exchange valve is switched again, the sample with the mobile phase fed by the pump units are supplied to the column.

In the UHLPC, several times sample processing ability is required under the several times ultra high pressure in comparison with the HPLC. Namely, a complex construction and several times durability are required for keeping the fluid-tight between the needle and the sample injection port under 60 to 120 M Pa condition. It is difficult to realize the above-mentioned construction.

Further, in the UHPLC, since the analysis time per one sample is short time of several ten seconds to several minutes, it is difficult to fully execute the flushing operation of the mobile phase in the needle. Namely, it is difficult for reducing the carry over of a sample due to the principle of the UHPLC.

Therefore, the automatic sample introduction unit of the loop injection system is suitable for the UHPLC.

PRIOR ART LITERATURE

Patent Documents

Patent Document 1: JP-H01-248055-A
Patent Document 2: JP-2006-292641-A
Patent Document 3: JP-H06-235722-A

SUMMARY OF THE INVENTION

Problems to be Solved by the Invention

In case that the sample introduction unit of the loop injection system is used for the UHPLC, however, since a syringe executes the both operations of accounting the sample and washing the flow passage in a prior art, there are following problems in the prior art.

Firstly, the operation stroke number of the syringe per number of the analyses is numerous. As the result, the consumable syringe exchange frequency is extremely high, so that the reliability and durability of the apparatus is deteriorated.

Secondly, the high accuracy and high discrimination operation of the syringe is required at low flow rate (low speed) for sample accounting operation, and the high flow rate (high speed) operation of the syringe is required for the flow passage washing operation in order to reduce the washing time. The above-mentioned two requirements are conflict with each other, so that there is limit vale to satisfy the two requirements by using the operation of one syringe. Namely, when a small volume syringe is used for prior to sample quantity accounting, the washing time grows longer and the cycle time grows longer. The problem is happened. On the other hand, when a large volume syringe is used for prior to flow passage washing, the accuracy and discrimination of the operation of the syringe are deteriorated. As the result, the injection rate repeatability is lowered.

Thirdly, since washing system of the external wall of the needle is the dipping washing system only, the sample attached to the external wall of the needle cannot be washed fully. Therefore, it is one factor of carry-over of a sample.

An object of the present invention is to realize a liquid sample analyzing apparatus and a liquid sample introduction apparatus capable for processing a sample with high reliability at high speed.

Means for Solving the Problems

In order to achieve the object of the present invention, the present invention is constructed as follows:

In a liquid sample analyzing apparatus, a liquid sample introduction apparatus, and a liquid sample introducing system, an external wall of a needle sucking and discharging a liquid sample is inserted into a washing tank to wash the external wall, a liquid sample being sucked into the needle while the quantity of the liquid sample is accounted by using a syringe, the liquid sample sucked into the needle being supplied to a sample storage loop while the liquid sample sucked into the needle is accounted by using the syringe, the liquid sample stored in the sample storage loop being supplied to a mobile phase flow passage, the needle being separated from the syringe means, a washing solution being supplied from the washing solution supply means into the needle to wash the inner wall of the needle.

Effects of the Invention

The present invention can realize a liquid sample analyzing apparatus, a liquid sample introduction apparatus, and a liquid sample introduction system capable for processing a sample with high reliability at high speed.

MODES FOR CARRYING OUT THE INVENTION

Hereunder, embodiments of the present invention will be described with reference to the accompanying drawings.

Embodiment

Figure 1:
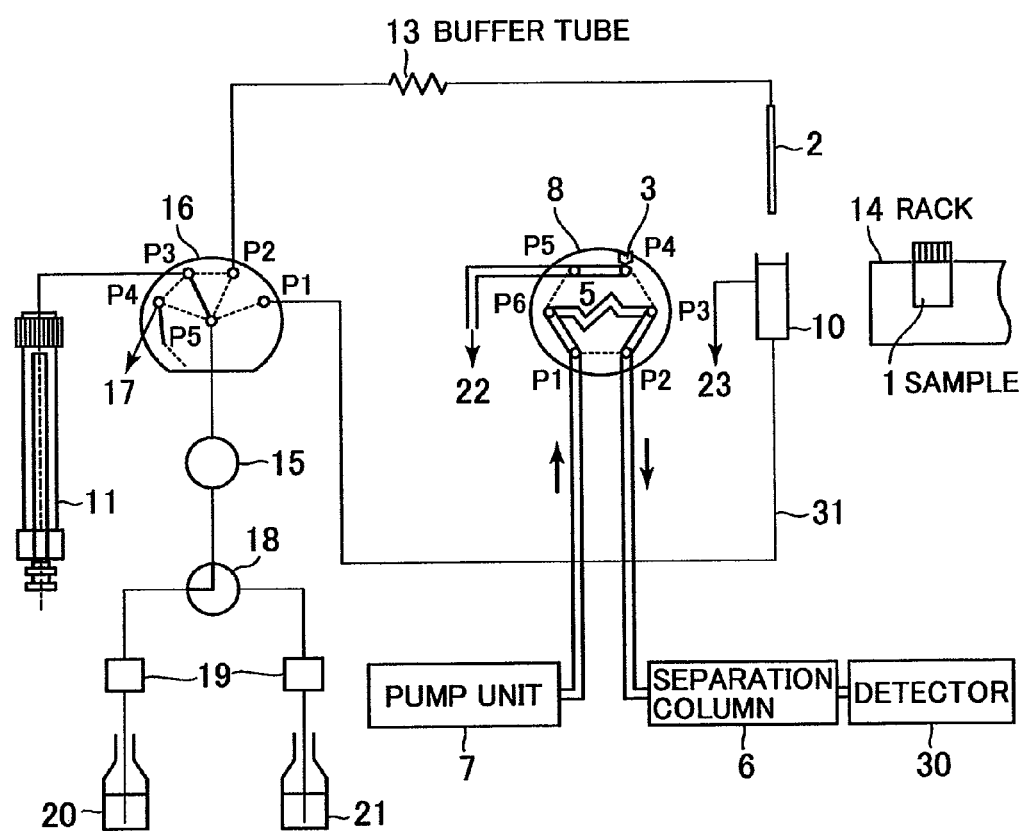
FIG. 1 is a drawing showing a schematic construction and an idling condition of a liquid chromatograph apparatus according to the first embodiment of the present invention.
Figure 43:
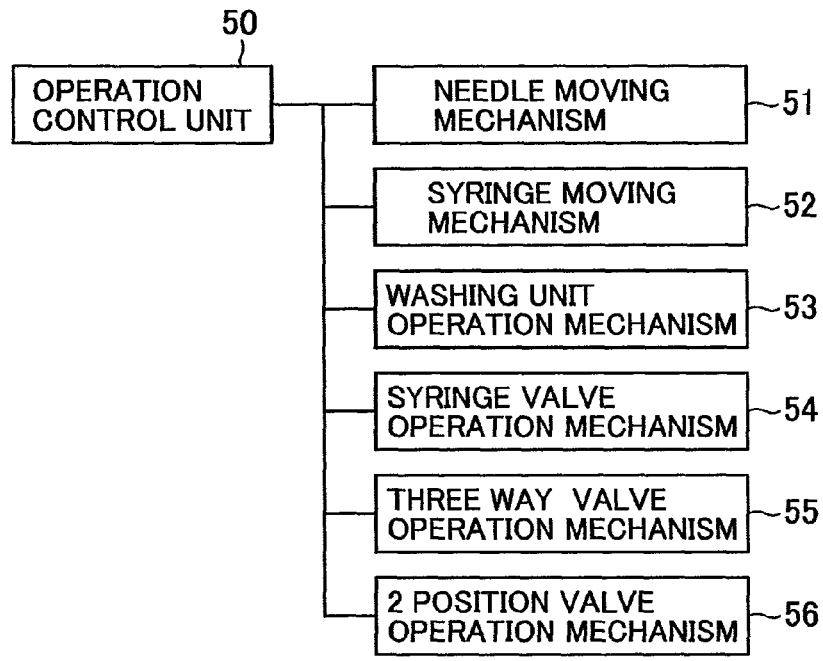
FIG. 43 is an operation control function block diagram of each of the first to fifth embodiments of the present invention.

FIG. 1 is a showing a schematic construction of a liquid chromatograph apparatus using a loop injection system automatic sample introduction apparatus of the first embodiment of the present invention, FIGS. 2 to 11 being diagrams showing the details of a sample injection step of the first embodiment of the present invention. Further, FIG. 43 is an operation control block diagram of the embodiment of the present invention.

In FIG. 1, a sample hold container 1 is set on a sample rack 14. A needle 2 is moved between the sample hold container 1, a washing tank 10, and a sample injection port 3 of the 6-port 2-position valve (a first flow passage exchange means) 8 by a needle moving mechanism 51. The needle moving mechanism 51 is controlled by an operation control unit 50.

In the 6-port 2-position valve 8, a port P1 is connected to a pump unit 7, a port P2 being connected to a separation column 6, a port P4 being connected to the sample injection port 3, a port P5 being connected to a drain 22, a sample storage loop 5 being connected between a port P3 and P6. The separation column 6 is connected to a detector 30. The detector 30 detects and analyses a sample supplied from the separation column 6.

Further, the 6-port 2-position valve 8 can be set to two positions of an injection position communicating the ports P1-P6, P4-P5, and P2-P3 and a load position communicating the ports P1-P2, P3-P4, and P5-P6 by rotating the valve at 60 degrees.

A washing unit (a washing pump (a washing solution feeding means)) 15 is connected to a three way valve 18, the three way valve 18 being connected to a washing bottle 20 and a washing bottle 21 through a degassing unit (degasser) 19. The washing unit 15 can select one of a washing solutions A or a washing solution B to be fed to a 5-port 4-position valve (a second flow passage exchanging means) 16 by exchanging the three way valve 18 into the washing solution bottle 20 side or the washing solution bottle 21 side.

In the 5-port 4-position valve 16, the port P1 is connected to the washing tank 10 through a washing solution pipe 31, the port P2 being connected to a buffer pipe 13, the port P3 being connected to a syringe 11 which is a sample accounting means, the port P4 being connected to a plunger washing flow passage 17, the common port P5 being connected to the washing unit 15. The plunger washing flow passage 17 communicates the pump unit 7, washing salt, which is included in the mobile phase, deposited on the surface of the plunger of the pump unit 7 from the automatic sample introduction apparatus at need.

The 5-port 4-position valve 16 can be set to four positions of (1) communicating the ports P1-P5 and P2-P3, (2) communicating the ports P2-P5 and P3-P4, (3) communicating the ports P3-P5 and (4) communicating the ports P4-P5 by rotating the valve at 45 degrees at each of positions.

When the 5-port 4-position valve 16 is set to the position (1) that the port P1-P5 and the port P2-P3 are communicated with each other, the needle 2 is connected to the syringe 11, which is the accounting means, through the buffer pipe 13, and the needle 2 sucks and discharges a liquid by operating the syringe 11 up and down.

The movement, suction and injection operation of the syringe 11 are controlled by a syringe moving mechanism 52, the washing unit 15 being operated by a washing unit operation mechanism 53. Further, the syringe valve 16 is operated by a syringe valve operation mechanism 54, the three way valve 18 being operated by a three way valve operation mechanism 55, the two position valve 8 being operated by a two position operation valve mechanism 56.

Further, these operations of the syringe moving mechanism 52, the washing unit operation mechanism 53, the syringe valve operation mechanism 54, the three way valve operation mechanism 55, and the two position valve operation mechanism 56 are controlled in accordance with the instruction signals from the operation control unit 50.

The liquid chromatograph apparatus as shown in FIG. 1 constructs a sample introduction apparatus used for the liquid chromatograph apparatus, except for the pump unit 7, the separation column 6, and the detector 30.

Namely, the sample introduction apparatus used for the liquid chromatograph apparatus includes the syringe 11, the valve 16, the washing unit 15, the three way valve 18, the degasser 19, the buffer pipe 13, the needle 2, the injection valve 8, the washing tank 10, and the washing solution tank 31.

Next, the sample injection step of the first embodiment of the present invention will be described with reference to FIGS. 1 to 12.

In the loop injection system according to the first embodiment, the needle 2 sucks the sample whose quantities are large volume in comparison with the actual volume to be discharged into the mobile phase flow passage, the front edge portion and the rear end portion of the corresponding to the washing solution part in the sucked sample being cut, only the center portion of the sucked sample being fed to the column. This system is so called a cut type system. The detailed description of each step of the cut type system will be described herein under, and the agreement of the definitions of terms will be described as follows:

$vi$: injection volume (net sample introduction volume to the mobile phase flow passage), $vl$: lead volume (cut volume), $vr$: rear volume (cut volume), $vd$: dead volume from the sample injection port to the injection valve, $va$: air volume (volume of the air layer in front and rear of a sample).

In the automatic sample introduction apparatus, it can be selected whether or not the air volume $va$ is arranged in front of the sample and the rear of the sample.

FIG. 1 is a drawing to show the flow passage of the idle condition after the initializing operation of the automatic sample introduction apparatus. The mobile phase flows into the separation column 6 from the pump unit 7 through the sample storage loop 5 of the 6-port 2-position valve 8. The washing solution bottle 20 is connected to the syringe 11 through the three way valve 18, the washing unit 15, and the port 3 of the 5-port 4-position valve 16. The needle 2 is positioned above the washing tank 10 (the needle 2 is opposite to the opening portion of the washing tank 10).

Figure 2:
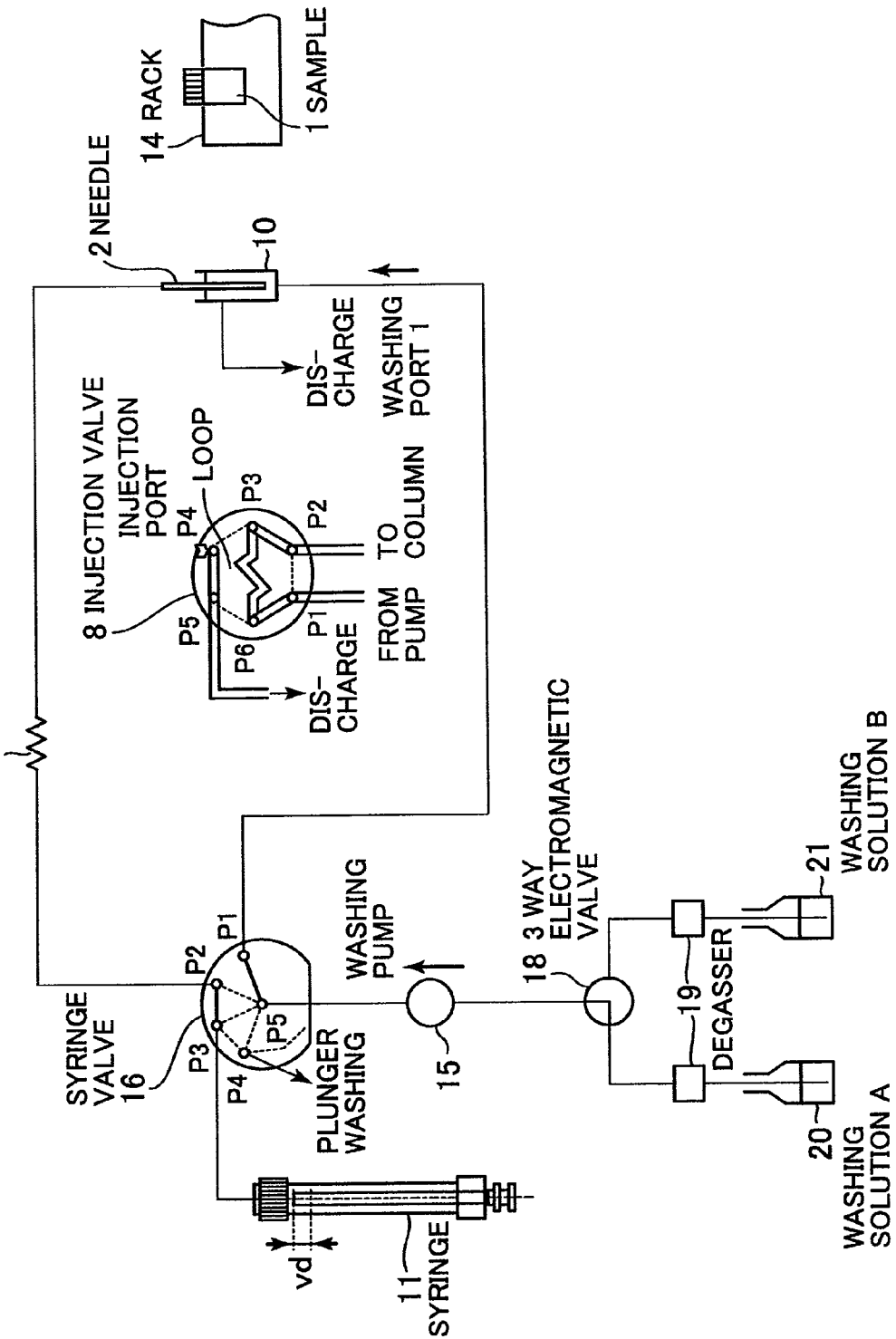
FIG. 2 is a drawing showing a schematic construction and a step for a washing solution suction of a syringe and for washing an external wall of a needle of the liquid chromatograph apparatus according to the first embodiment of the present invention.

FIG. 2 is a drawing to show the step for sucking the washing solution A from the washing solution bottle A 20 and the step for washing the external wall of the needle 2 in the washing tank 10. In FIG. 2, the syringe 11 sucks the dead volume $vd$ of the washing solution A. After the syringe 11 sucked the washing solution A, the 5-port 4-position valve 16 is rotated at 90 degrees in the clockwise direction to exchange the position into communicating position of (1) the ports P1-P5 and P2-P3, so that the needle is connected to the syringe 11 through the buffer pipe 13. The needle 2 is moved into the washing tank 10, the washing solution A being fed to the washing tank 10 by the washing unit 15 to wash the external wall of the needle 2 (washing operation prior to the sample suction operation).

Figure 3:
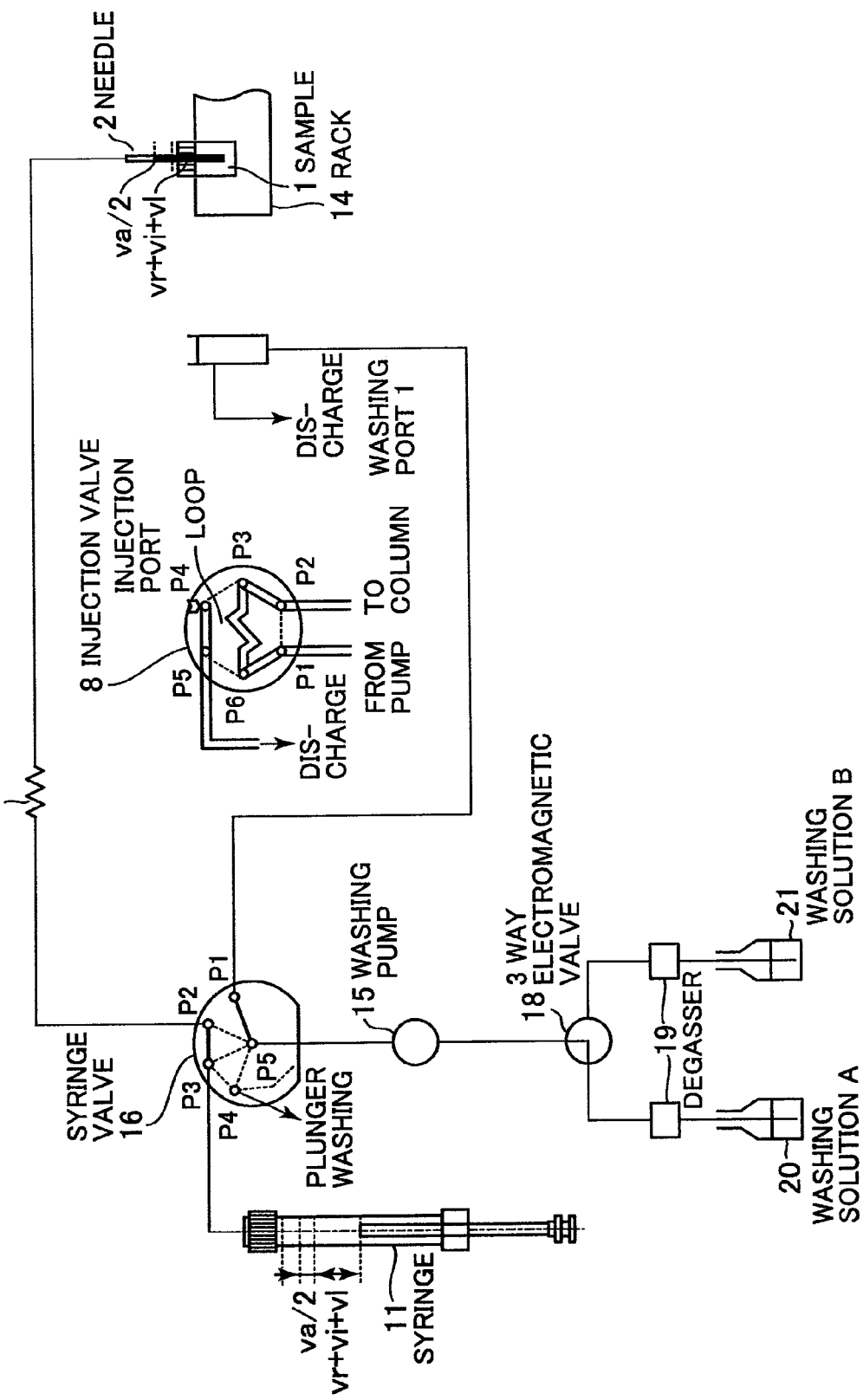
FIG. 3 is a drawing showing a schematic construction and a sample suction step of the liquid chromatograph apparatus according to the first embodiment of the present invention.

FIG. 3 is a drawing to show the sample sucking step. In FIG. 3, the syringe 11 sucks the air in volume of the half of the air volume $va/2$ during the operation of moving the needle for the sample hold container 1. The syringe 11 sucks the sample in the volume of $vr+vi+vl=$rear volume+injection volume+lead volume of the sample after the syringe 11 is moved in the sample hold container 1.

Figure 4:
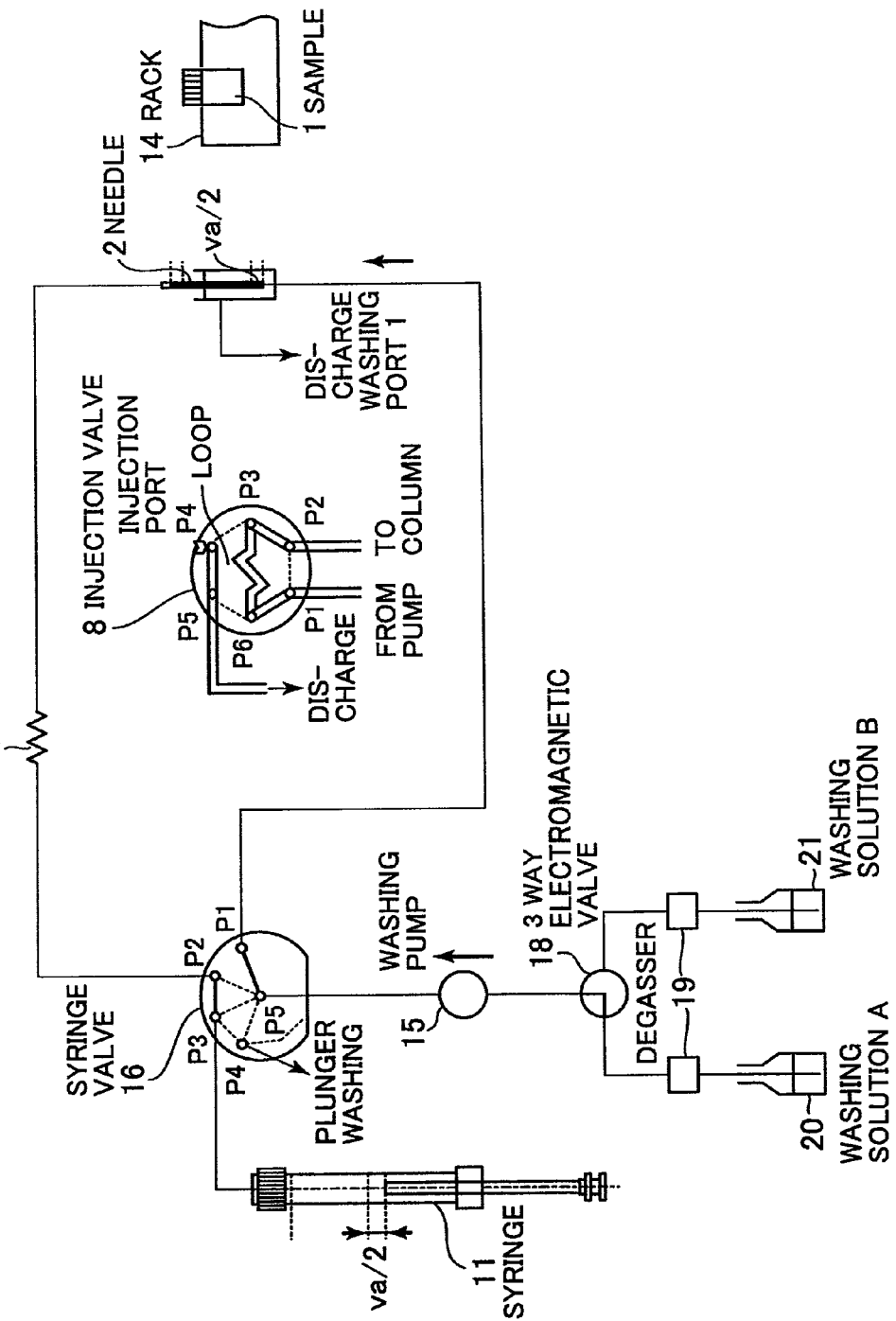
FIG. 4 is a drawing showing a schematic construction and a step for washing the external wall of a needle of the liquid chromatograph apparatus according to the first embodiment of the present invention.

FIG. 4 is a drawing to show the flow passage at the step for washing the external wall of the needle 2 in the washing tank 10 by means of the washing solution A. In FIG. 4, the syringe 11 sucks the half volume $va/2$ of the air volume during the operation for moving the needle 2 into the washing tank 10. After the needle 2 is moved in the washing tank 10, the washing unit 15 feeds the washing solution A to the washing tank 10 to wash the external wall of the needle 2 (washing after the sample sucking operation).

Figure 5:
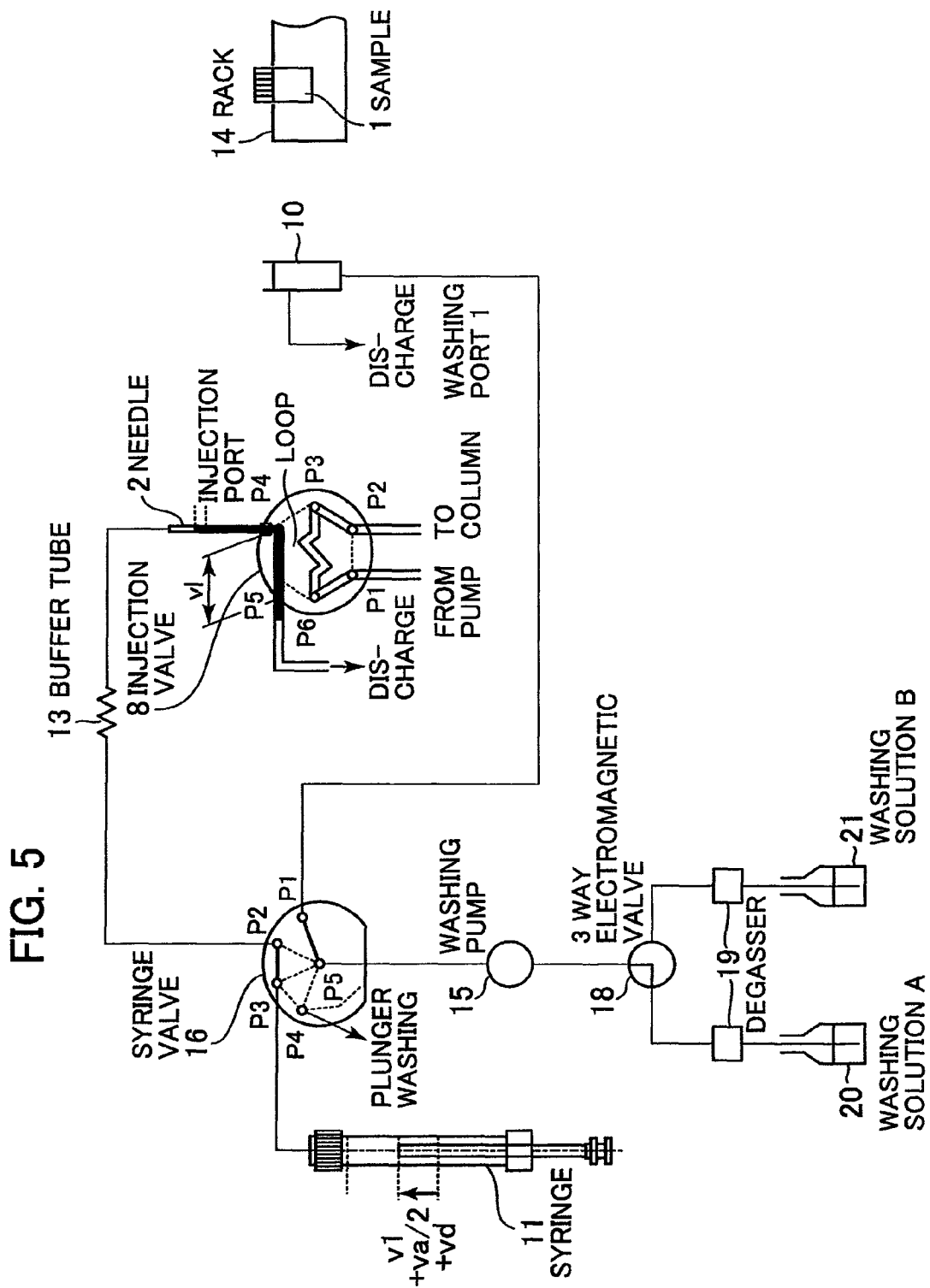
FIG. 5 is a drawing showing a schematic construction and a step for discharging a lead volume from the needle of the liquid chromatograph apparatus according to the first embodiment of the present invention.

FIG. 5 is a drawing to show the flow passage at the step for moving the needle 2 to the sample injection port 3 (the port P4) of the injection valve 8 and for discharging the lead volume of the sample. In FIG. 5, the needle 2 is moved to the sample injection port 3. The syringe 11 discharges the washing solution in volume of $vl+va/2+vd=$lead volume+air volume+dead volume, feeding the sample into the 6-port 2-position valve 8.

Figure 6:
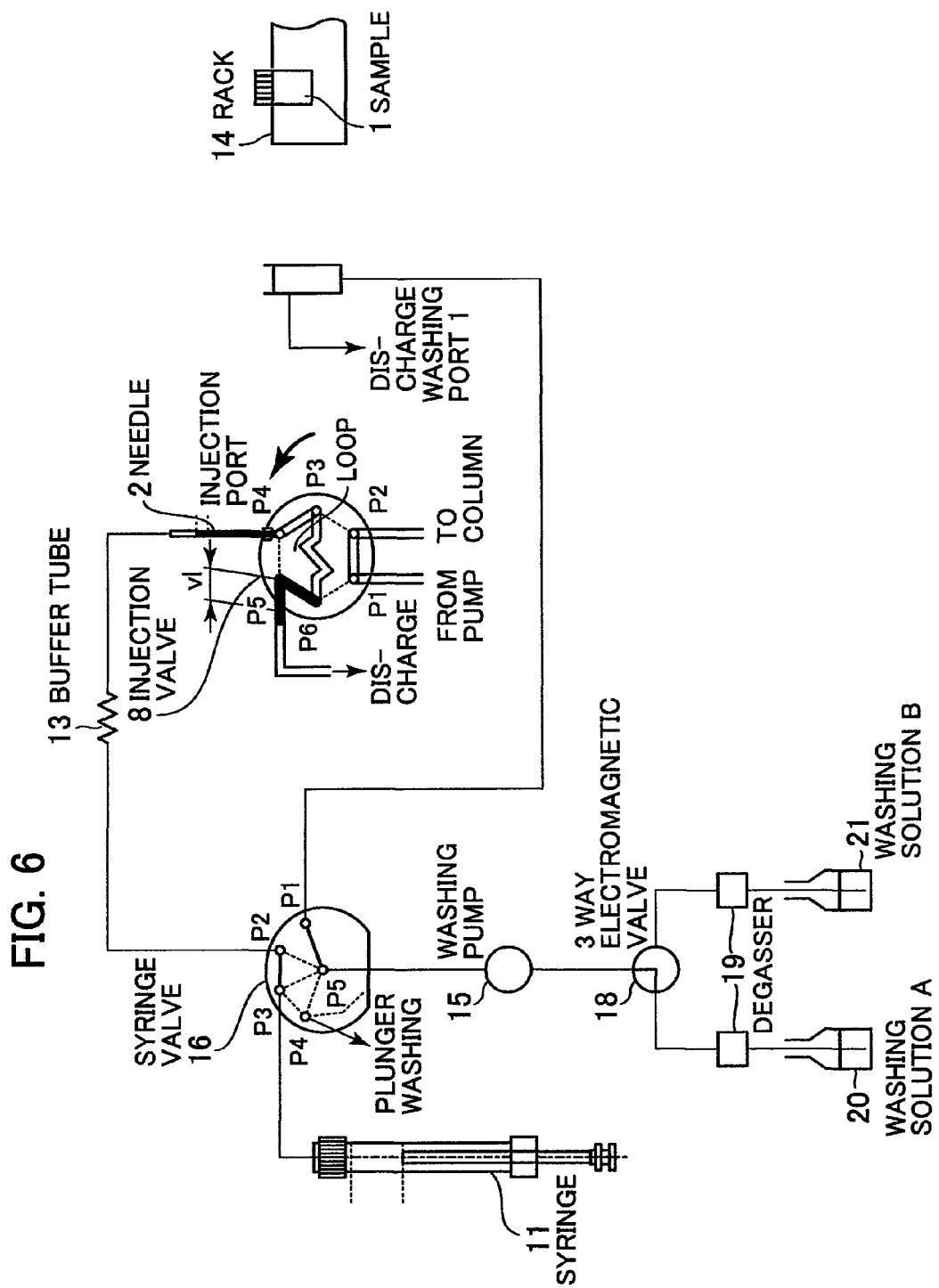
FIG. 6 is a drawing showing a schematic construction and a step for separating a sample storage loop from a mobile phase flow passage to decreasing the pressure of the liquid chromatograph apparatus according to the first embodiment of the present invention.

FIG. 6 is a drawing to show the flow passage at the pressure decreasing step for separating the sample storage loop 5 of the injection valve 8 from the mobile phase flow passage. In FIG. 6, the 6-port 2-position valve 8 is rotated at 60 degrees in counterclockwise direction, so that the sample storage loop 5 under high pressure condition is separated from the mobile phase flow passage, and the pressure loaded to the solvent in the sample storage loop 5 is released at the atmospheric pressure through the drain 22.

Figure 7:
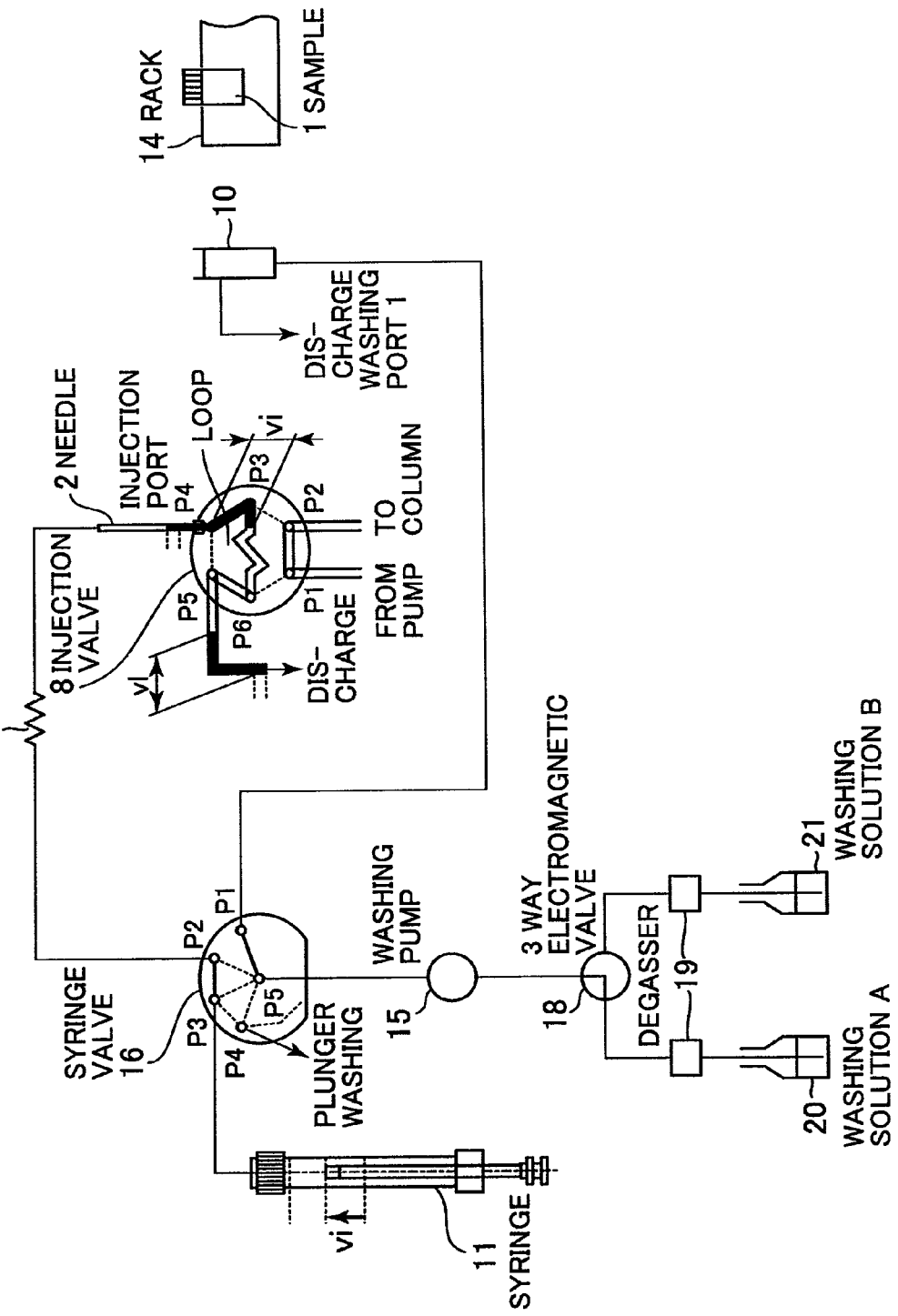
FIG. 7 is a drawing showing a schematic construction and a step for feeding a sample to a sample storage loop of the liquid chromatograph apparatus according to the first embodiment of the present invention.

FIG. 7 is a drawing to show the flow passage at the step for loading a sample. In FIG. 7, the syringe 11 discharges the washing solution in volume of vi=injection volume of the washing solution to feed the sample in the sample storage loop 5.

Figure 8:
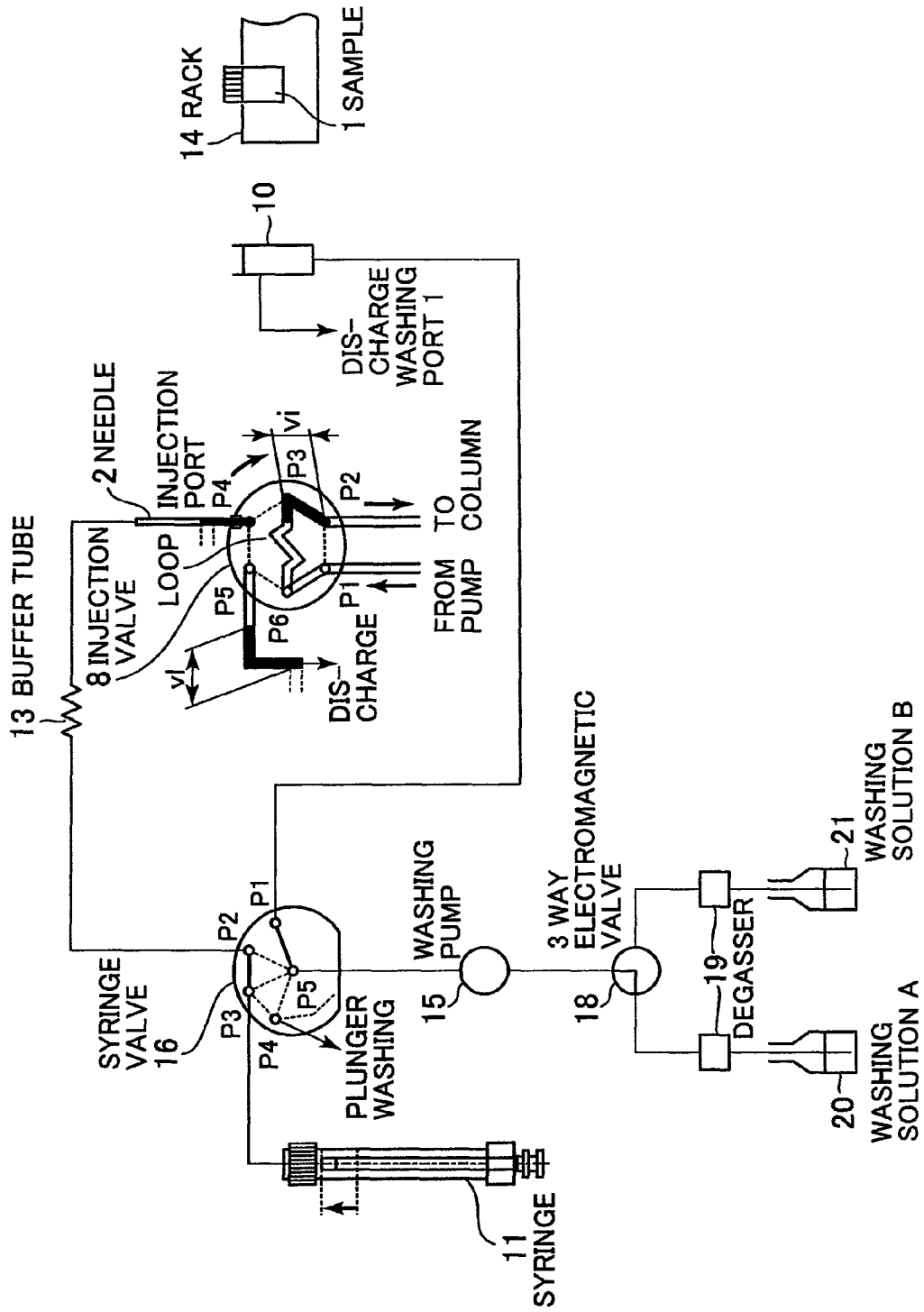
FIG. 8 is a drawing showing a schematic construction and a step for feeding a sample in a mobile phase flow passage a sample storage from the sample storage loop of the liquid chromatograph apparatus according to the first embodiment of the present invention.

FIG. 8 is a drawing to show the flow passage at the step for discharging the sample. In FIG. 8, the 6-port 2-position valve 8 is rotated at 60 degrees in the clockwise direction, so that the sample storage loop 5 is connected to the pump unit 7 and the separation column 6 to introduce the sample into the mobile phase flow passage. The syringe 11 is moved to a top dead center after the exchange of the condition of the 6-port 2 position valve 8.

Figure 9:
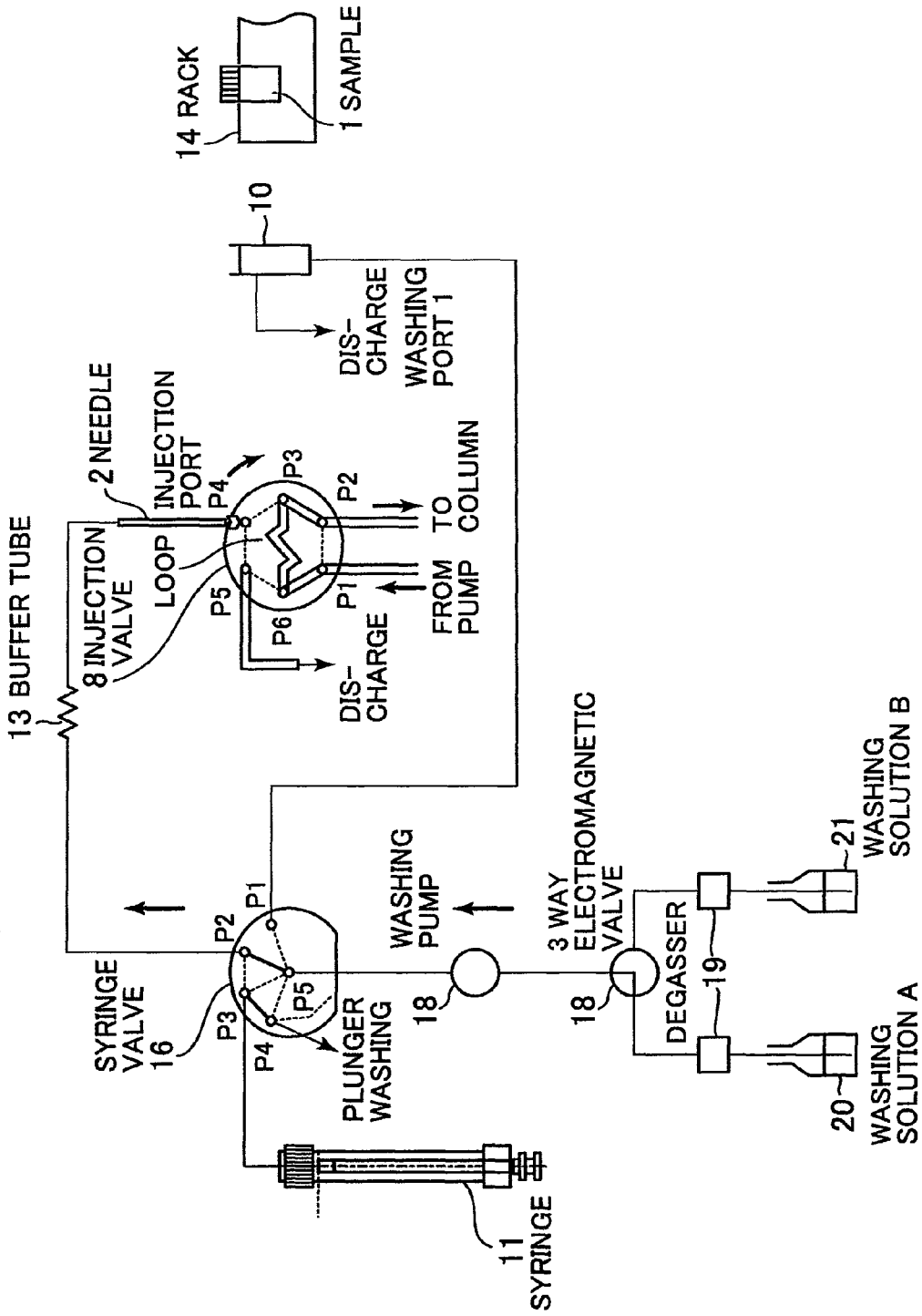
FIG. 9 is a drawing showing a schematic construction and a step for washing the inner wall of the needle of the first embodiment of the present invention.

FIG. 9 is a drawing to show the flow passage at the step for washing the inner wall of the needle 2 by means of the washing solution A. In FIG. 9, the 5-port 4-position valve 16 is rotated at 45 degrees in the counterclockwise direction, being exchanged into to position (2) to communicate the ports P2-P5 and the ports P3-P4 to feed the washing solution A by means of the washing unit 15. The flow passages in the buffer pipe 13, needle 2, the sample injection port 3 (port P4), and the 6-port 2-position valve 8 are washed by means of the washing solution A, and the washing solution A is discharged to the drain 22.

Figure 10:
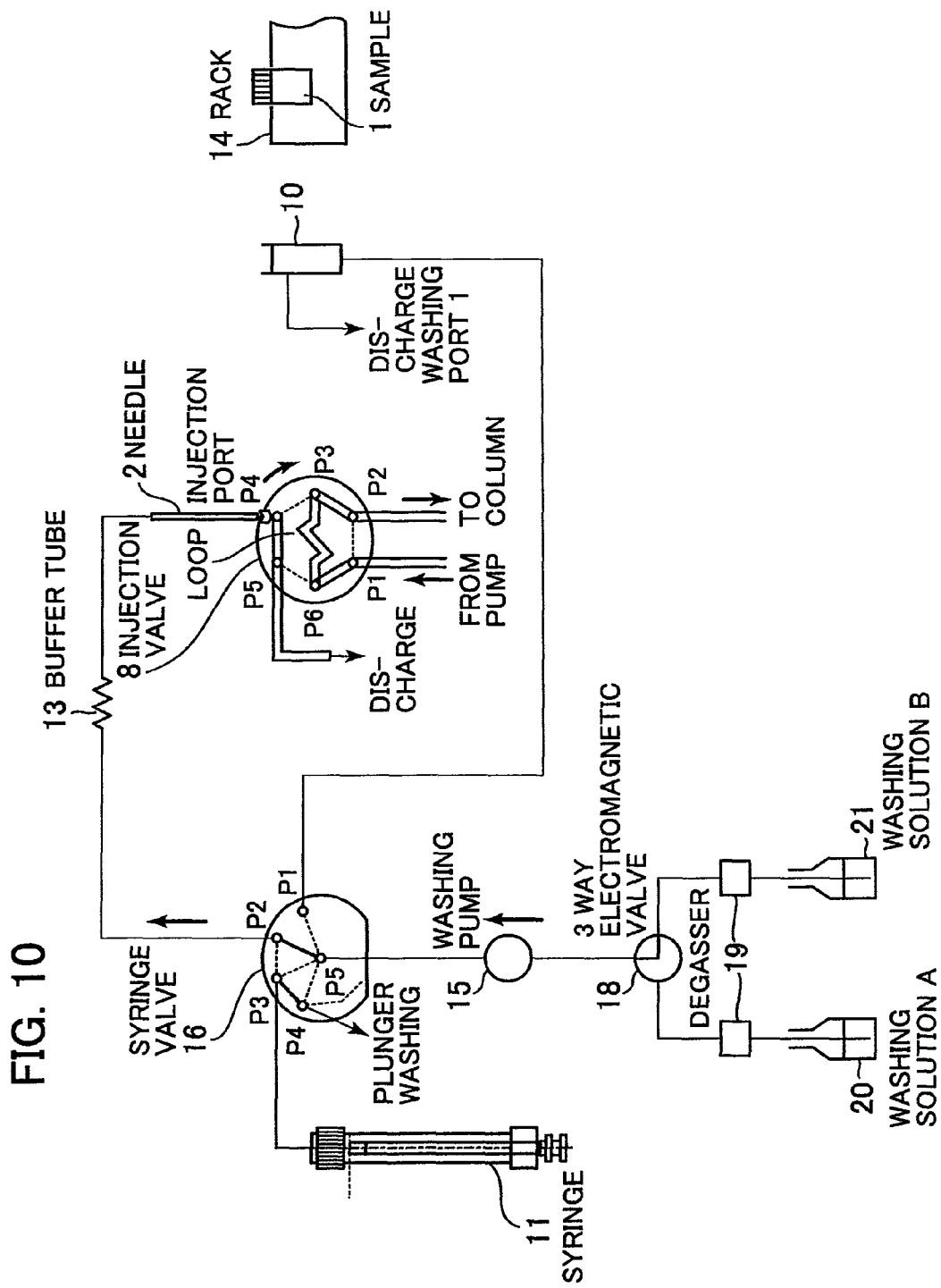
FIG. 10 is a drawing showing a schematic construction and a step for washing the inner wall of the needle of the first embodiment of the present invention.

FIG. 10 is a drawing to show the flow passage at the step for washing the inner wall of the needle 2 by means of the washing solution B. In FIG. 10, the three way valve 18 is exchanged to connect the washing solution bottle 21, the washing solution B being fed to the syringe valve 16 by means of the washing unit 15. The flow passages in the buffer pipe 13, needle 2, the sample injection port 3 (port P4), and the 6-port 2 position valve 8 are washed by means of the washing solution B, and the washing solution A is discharged to the drain 22.

After the washing operation is finished, the condition is shifted to the idling condition shown in FIG. 1. In order to shift the condition into the idling condition, the 5-port 4-position valve 16 is rotated at 45 degrees in the counterclockwise direction to exchange the position into the position (3) for communicating the ports P3-P5. The needle 2 is moved above the washing tank 10, the three way valve 18 being exchanged to connect the washing A solution bottle 20.

Figure 11:
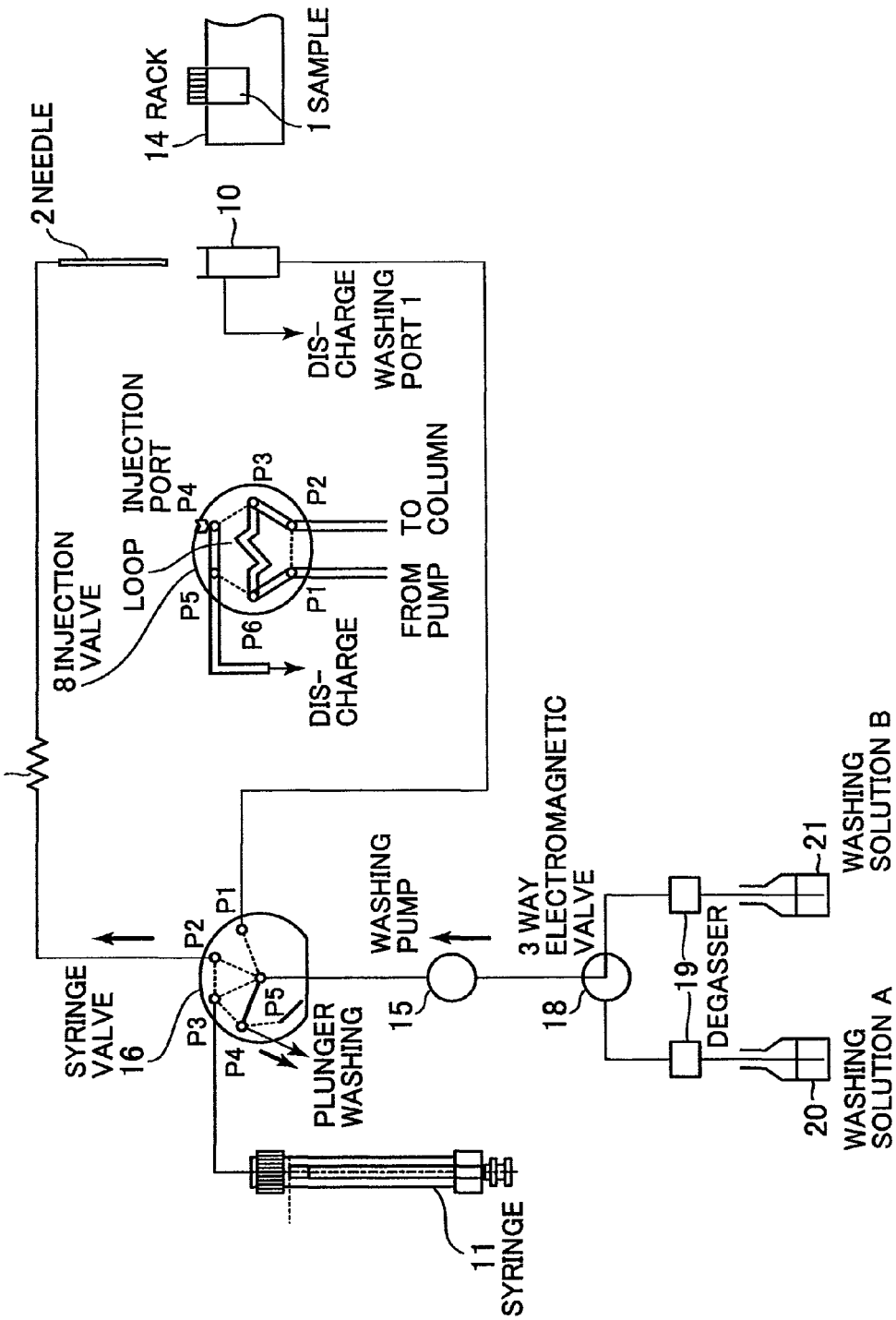
FIG. 11 is a drawing showing a schematic construction and a step for washing a plunger of the liquid chromatograph apparatus according to the first embodiment of the present invention.

FIG. 11 is a drawing to show the flow passage at the step for washing the plunger of the pump unit 7. In FIG. 11, the three way valve is exchanged to connect the washing solution bottle 21. The 5-port 4-position valve 16 is rotated at 45 degrees in the counter clockwise direction to exchange the position into the position (4) for communicating the ports P4-P5. The washing solution B is fed to the plunger washing flow passage 17 by means of the washing unit 15. The tree way valve 18 is not required to be exchanged in case of using the washing solution A. After the washing operation, the condition is shifted to the idling condition shown in FIG. 1.

As described above, according to the first embodiment of the present invention, the functions are divided into two functions of the syringe 11 accounting the sample and the washing unit 15 washing the flow passage, so that the following effects can be obtained.

Firstly, the number of the operation strokes of the syringe 11 can be reduced in comparison with the number of the analysis operations, so that the frequency of exchanging the syringe as a consumable material is reduced, and the reliability and the durability of the apparatus are improved.

Secondly, the flow passage washing time is reduced by the washing unit 15 capable for feeding a liquid at high flow rate (high speed), so the cycle time can be reduced. Further, the small volume syringe 11 is used, so that the syringe 11 can be operated at high accuracy and high discrimination, and the repeatability of the injection volume can be improved.

Thirdly, the external wall of the needle 2 is washed by flowing a washing solution, so that the effect for washing a sample attached to the external wall of the needle 2 can be improved, and the carry over of a sample can be reduced.

Namely, according to the first embodiment of the present invention, the present invention can be realize a liquid chromatograph apparatus and an automatic sample introduction apparatus used for a liquid chromatograph apparatus capable for improving the basic performance and for processing at high speed with a high reliability.

Next, the detailed sample injection step of the second embodiment of the present invention will be described with reference to FIGS. 12 to 18. The second embodiment is the example a liquid chromatograph apparatus using a loop injection system automatic sample introduction apparatus, as same as the first embodiment.

Further, the idling condition at the sample injection step is the same condition as shown in FIG. 1, so that the drawing of the idling condition is omitted. Further, the constructions of the apparatuses of the first and the second embodiments are equal with each other, the operation controls of the first and the second embodiments are different with each other.

The loop injection system according to the second embodiment is the system for feeding all sample sucked from the needle 2 into the sample storage loop 5 of the injection valve 8 to reach the sample at the separation column 6, and the system is called to all volume injection system. Herein under, the same terms of the first embodiment are used for detailed describing each step of the all volume injection system. However, the new term of vf=feed volume is defined.

The automatic sample introduction apparatus is initialized, the operation is started at the flow passage drawing of the idling condition (FIG. 1).

Figure 12:
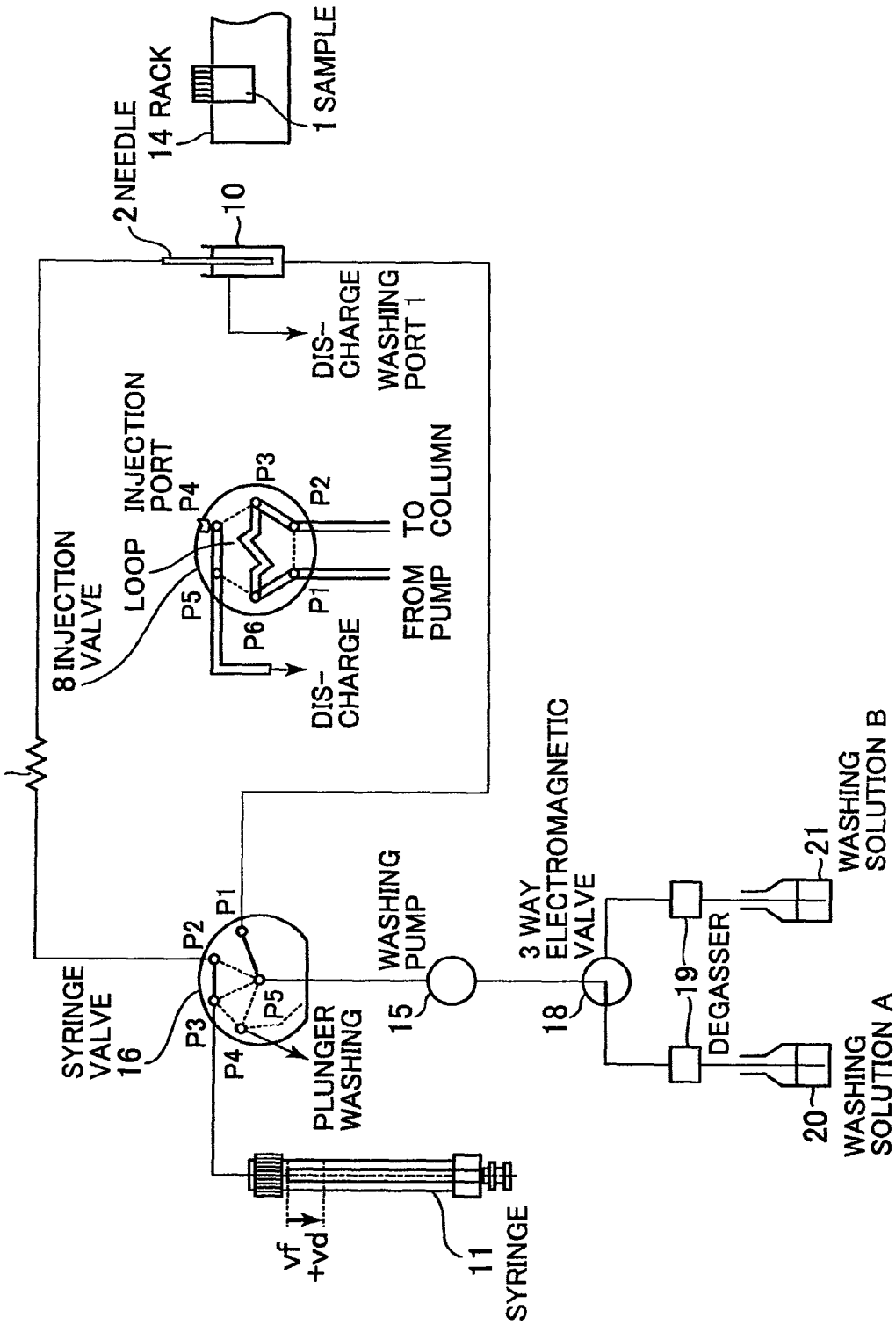
FIG. 12 is a drawing showing a schematic construction and a step for sucking the washing solution of the syringe and for washing the external wall of the needle of the liquid chromatograph apparatus according to the second embodiment of the present invention.

FIG. 12 is a drawing to show the flow passage at the step for sucking the washing solution A in the washing solution bottle 20 and for washing the external wall of the needle 2 in the washing tank 10.

In FIG. 12, the syringe 11 sucks the washing solution A in volume of vf+vd=feed volume+dead volume. After the syringe 11 sucks the washing solution A, the 5-port 4-position valve 16 is rotated at 90 degrees in the clockwise direction to exchange the position to the position of (1) communicating the ports P1-P5 and the ports P2-P3, so that the needle 2 is connected to the syringe 11 through the buffer pipe 13.

Further, the needle 2 is moved to the washing tank 10, the washing solution A being fed by the washing unit 15 to wash the external wall of the needle 2 (washing operation prior to the sample sucking operation).

Figure 13:
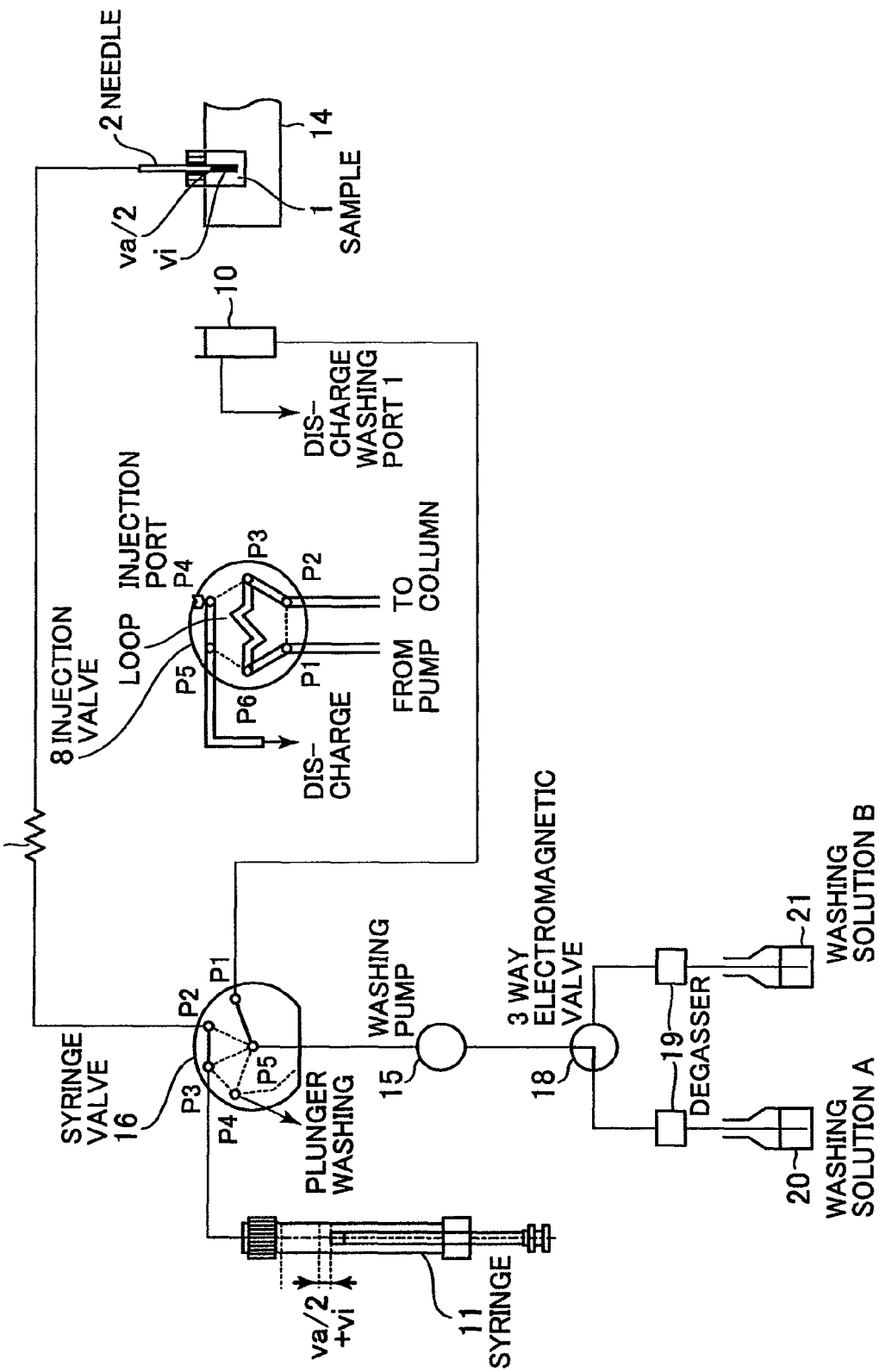
FIG. 13 is a drawing showing a schematic construction and a step for sucking a sample of the liquid chromatograph apparatus according to the second embodiment of the present invention.

FIG. 13 is a drawing to show the step for sucking the sample. In FIG. 13, the syringe 11 sucks the half (va/2) of the air volume during the operation for moving the needle 2 to the sample hold container 1. After the needle 2 is moved in the sample hold container 1, the syringe 11 sucks the sample in volume of injection volume (vi).

Figure 14:
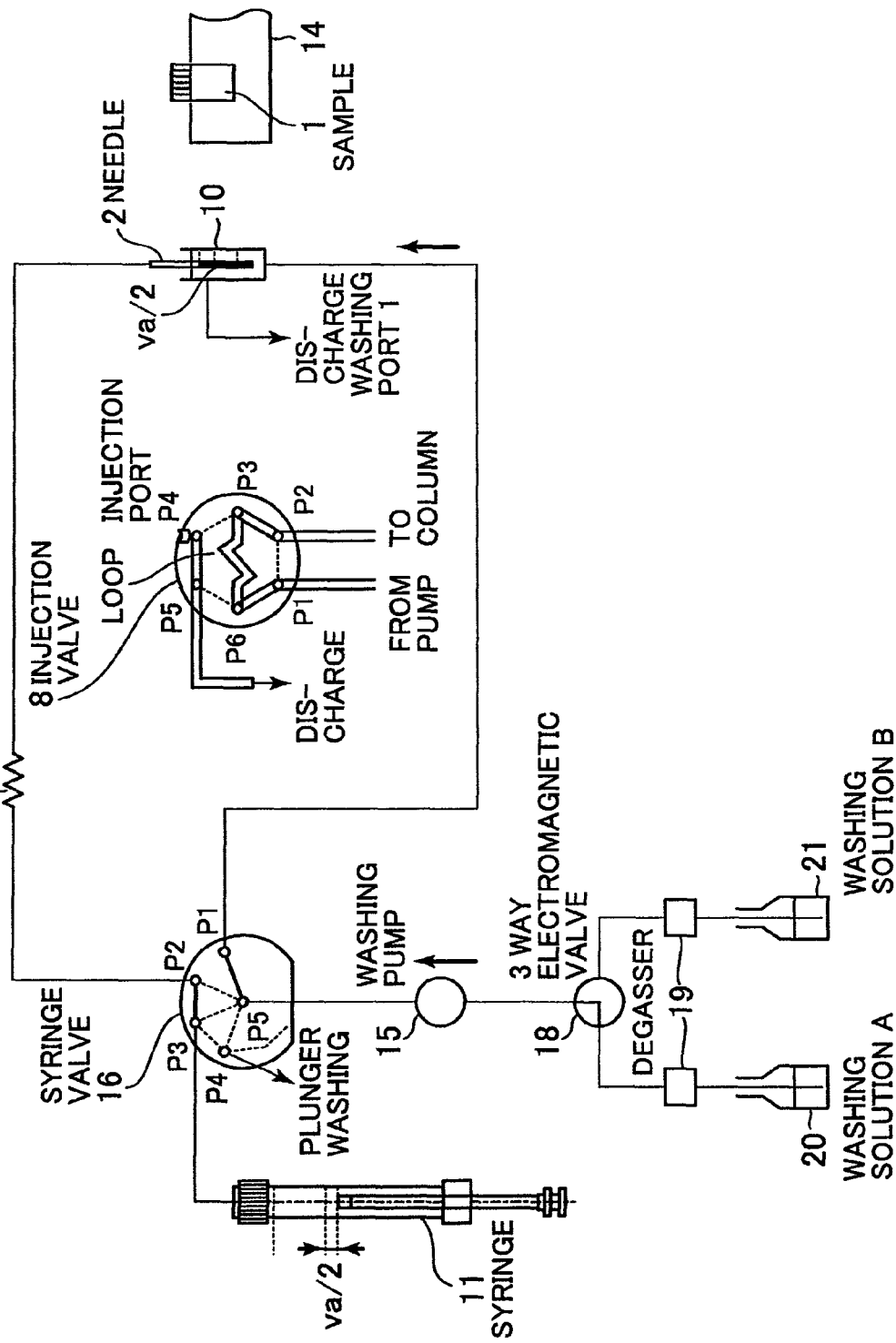
FIG. 14 is a drawing showing a schematic construction and a step for washing the external wall of a needle of the liquid chromatograph apparatus according to the second embodiment of the present invention.

FIG. 14 is a drawing to show the flow passage at the step for washing the external wall of the needle 2 in the washing tank 10 by using the washing solution A. In FIG. 14, the syringe 11 sucks the sir in volume of the half (va/2) of the air volume during the operation for moving the needle 2 to the washing tank 10. After the needle 2 is moved in the washing tank 10, the washing solution A is fed to the washing tank 10 by the washing unit 15 to wash the external wall of the needle 2 (washing operation after the sample sucking operation).

Figure 15:
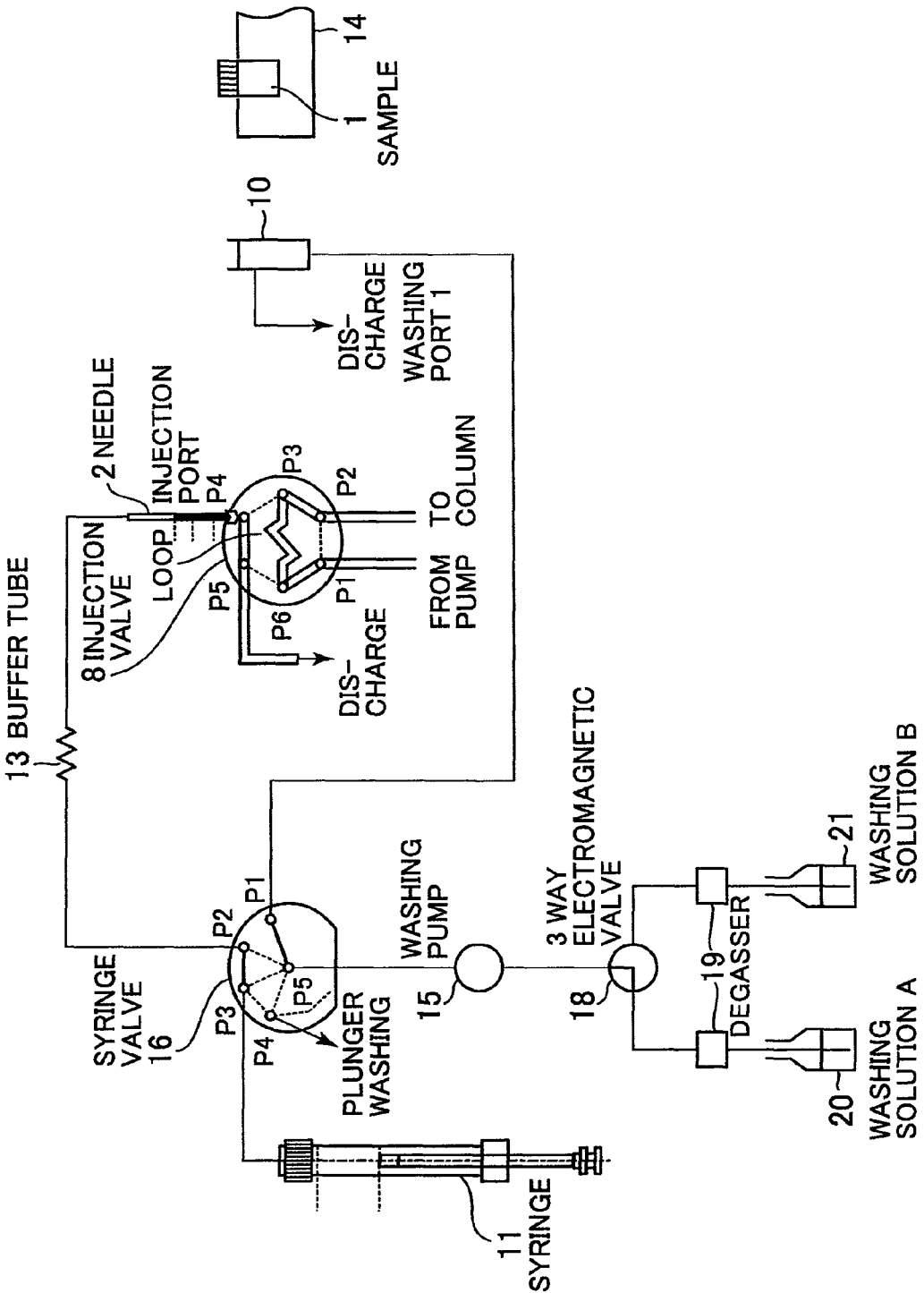
FIG. 15 is a drawing showing a schematic construction and a step for moving the needle for the sample injection port of the liquid chromatograph apparatus according to the second embodiment of the present invention.

FIG. 15 is a drawing to show the flow passage at the moving step for the sample injection port 3 (port P4) of the injection valve 8. In FIG. 15, the needle 2 is moved to the sample injection port 3 (port P4) of the injection valve 8.

Figure 16:
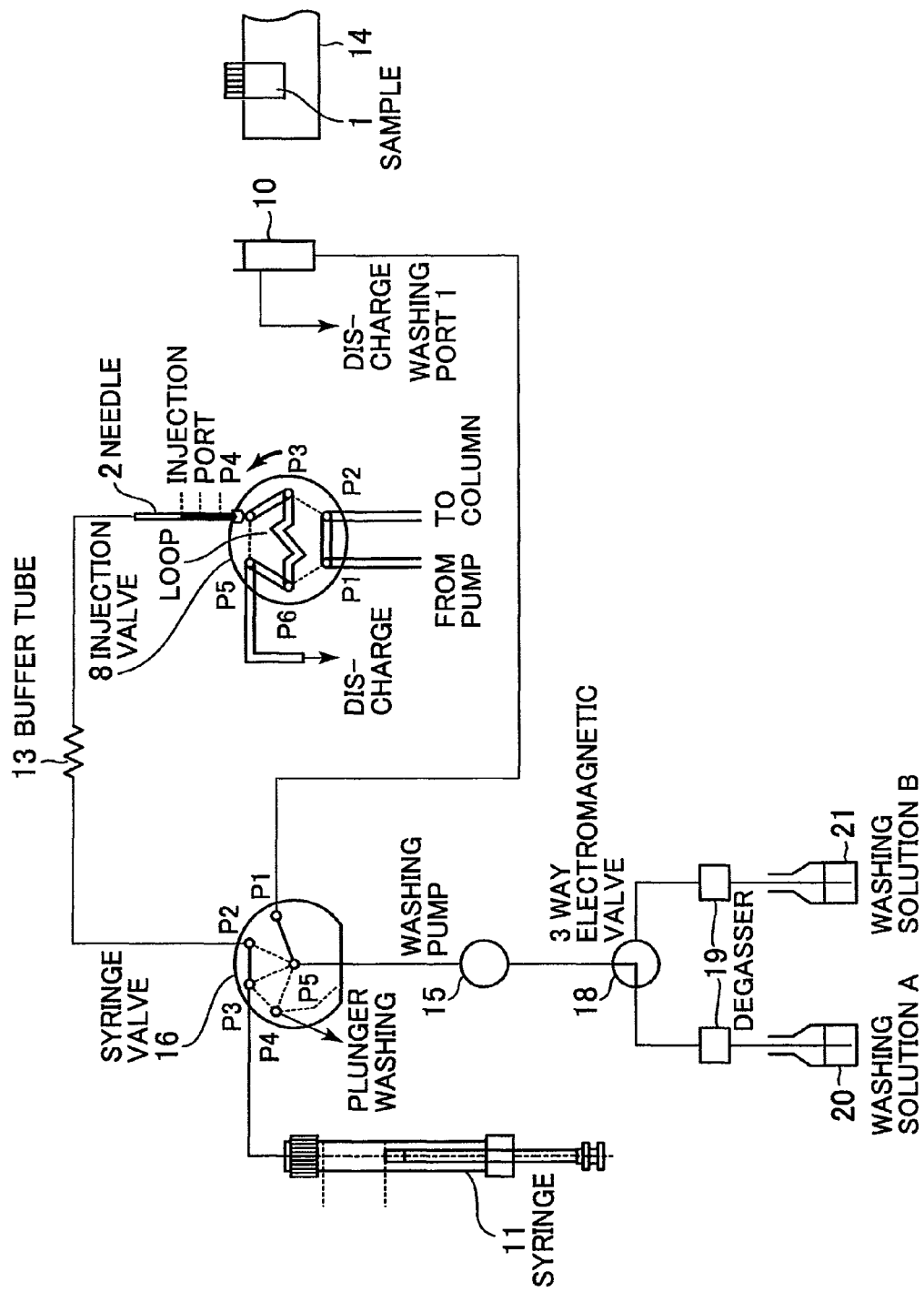
FIG. 16 is a drawing showing a schematic construction and a step for separating the sample storage loop from the mobile phase flow passage and for decreasing the pressure of the sample storage loop of the liquid chromatograph apparatus according to the second embodiment of the present invention.

FIG. 16 is a drawing to show the flow passage at the pressure decreasing step for separating the sample storage loop 5 of the injection valve 8 from the mobile phase flow passage. In FIG. 16, the injection valve 8, which is a 6-port 2-position valve, is rotated at 60 degrees in counter clockwise direction, so that the sample storage loop 5 under high pressure is separated from the mobile phase flow passage, and the pressure added to the solvent in the sample storage loop 5 is released at the atmospheric pressure through the drain 22.

Figure 17:
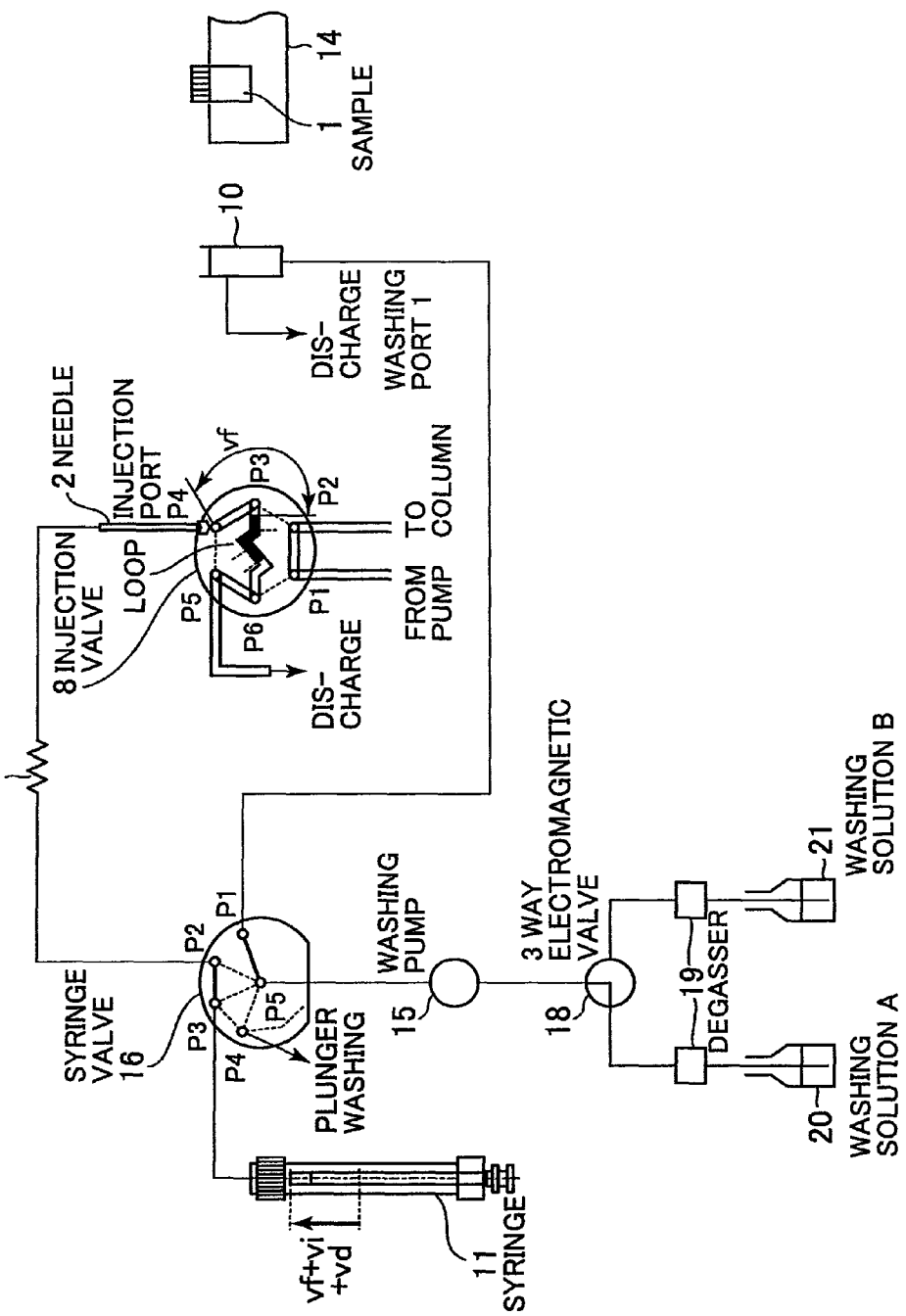
FIG. 17 is a drawing showing a schematic construction and a step for feeding the sample to the sample storage loop of the liquid chromatograph apparatus according to the second embodiment of the present invention.

FIG. 17 is a drawing to show the flow passage at the step for loading the sample. In FIG. 17, the syringe 11 discharges the sample in volume of vf+vi+vd=feed volume+injection volume+dead volume, so that the sample is fed into the sample storage loop 5. All quantity of the sample of the injection volume (vi) sucked from the needle 2 is held in the sample storage loop 5.

Figure 18:
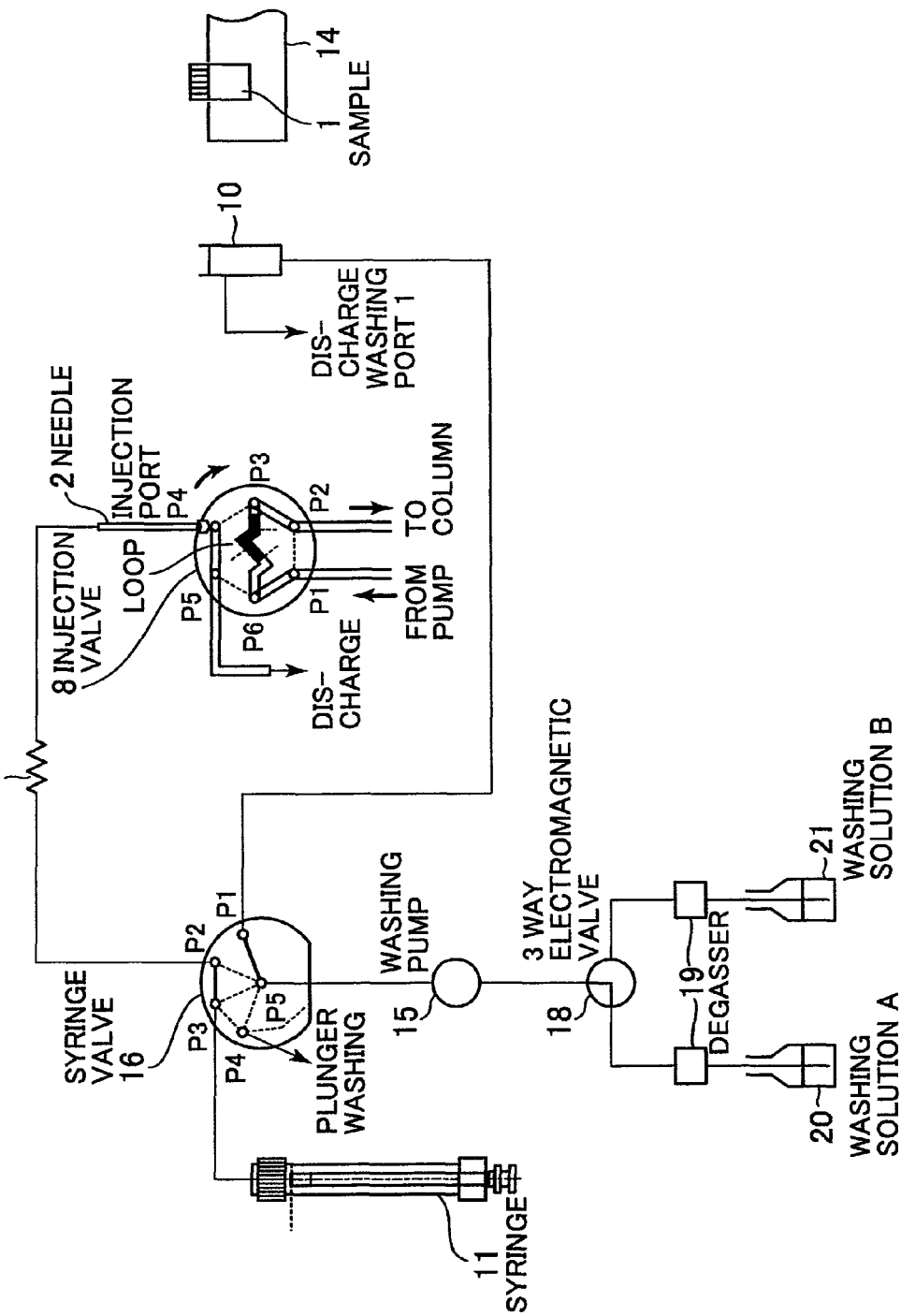
FIG. 18 is a drawing showing a schematic construction and a step for feeding the sample into the mobile phase flow passage from the sample storage loop of the second embodiment of the present invention.

FIG. 18 is a drawing to show the step for discharging the sample. In FIG. 18, the 6-port 2-position valve 8 is rotated at 60 degrees in clockwise direction, so that the sample storage loop 5 is connected to the pump unit 7 and the separation column 6, and the sample is introduced into the mobile phase flow passage. After exchanging the 6-port 2-position valve 8, the syringe 11 is moved to the top dead center.

Herein under, the washing step according to the all volume injection system is equal to the step as shown in FIGS. 1 to 11.

The second embodiment of the present invention can also realize the liquid chromatograph apparatus and the automatic sample introduction apparatus used for the liquid chromatograph apparatus capable for improving the basic performance and for executing the processes at high sped and high reliability, as same as the first embodiment.

Next, the sample injection step of the third embodiment of the present invention will be described with reference to FIGS. 19 to 25. The second embodiment is an example of a liquid chromatograph apparatus using a loop injection system automatic sample introduction apparatus, as same as the first embodiment.

Further, the idling condition at the sample injection step is the same condition as shown in FIG. 1, so that the drawing of the idling condition is omitted. Further, the constructions of the apparatuses of the first and the third embodiments are equal with each other, the operation controls of the first and the third embodiments are different with each other.

The loop injection system according to the third embodiment is the system that the needle 2 sucks a sample having amount larger than the quantities to be actually discharged to the mobile phase flow passage, and the sample storage loop 5 is overflown at the sample injection operation to feed the volume of the loop capacity to the separation column 6, and the system is called a full loop system. Herein under, the same terms of the first embodiment are used for detailed describing each step of the full loop system. However, the new term of vw=waste volume is defined.

The automatic sample introduction apparatus is initialized, the operation is started at the flow passage drawing of the idling condition (FIG. 1).

Figure 19:
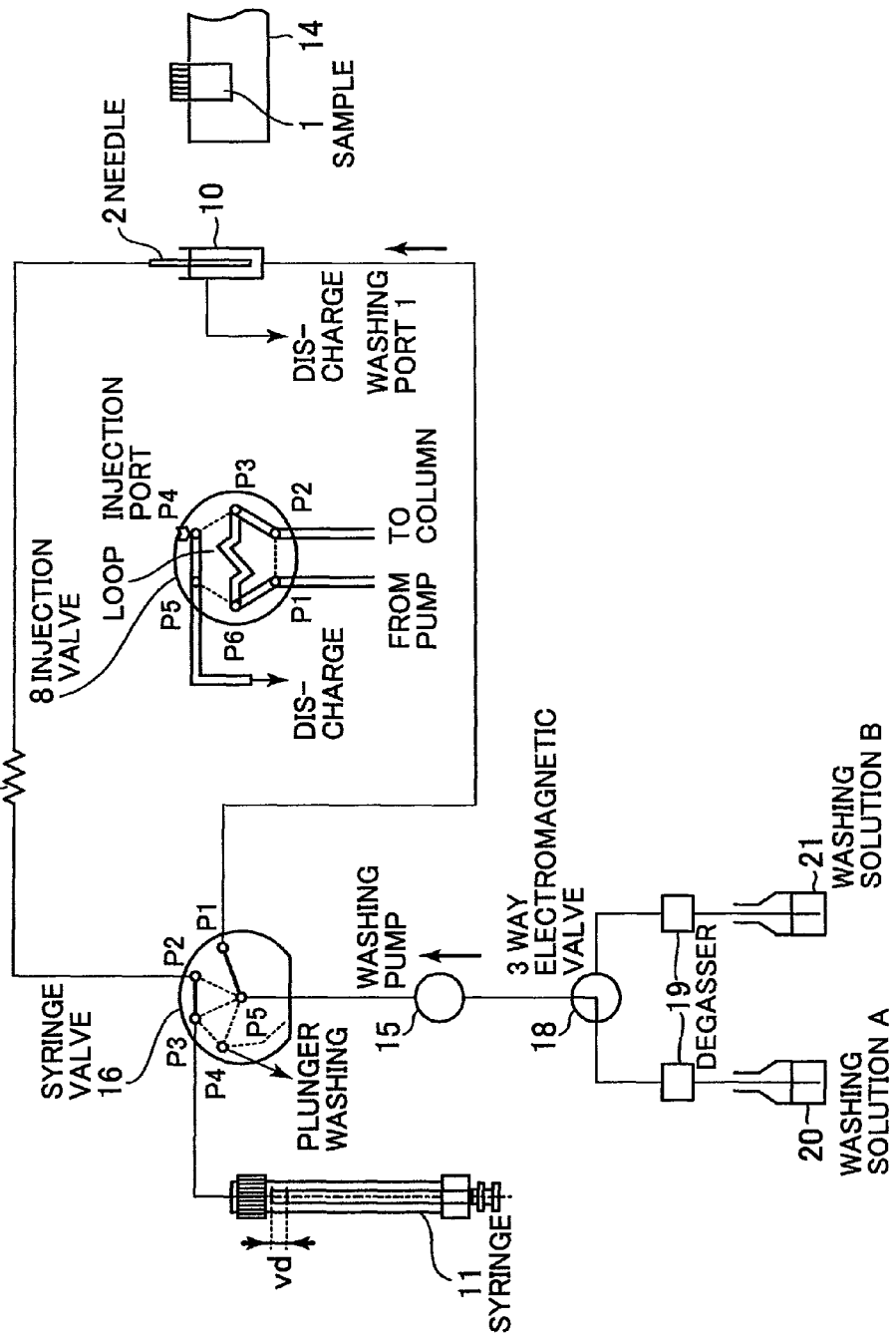
FIG. 19 is a drawing showing a schematic construction and a step for sucking the washing solution of the syringe and for washing the external wall of the needle of the liquid chromatograph apparatus according to the third embodiment of the present invention.

FIG. 19 is a drawing to show the flow passage at the step for sucking the washing solution A in the washing solution bottle 20 and for washing the external wall of the needle 2 in the washing tank 10. In FIG. 19, the syringe 11 sucks the washing solution A in volume of the dead volume. After sucking the washing solution A, the 5-port 4-position valve 16 is rotated at 90 degrees in the clockwise direction to exchange the position to the position of (1) communicating the ports P1-P5 and the ports P2-P3, so that the needle 2 is connected to the syringe 11 through the buffer pipe 13. The needle 2 is moved to the washing tank 10, the washing solution A being fed by the washing unit 15 to wash the external wall of the needle 2 (washing operation prior to the sample sucking operation).

Figure 20:
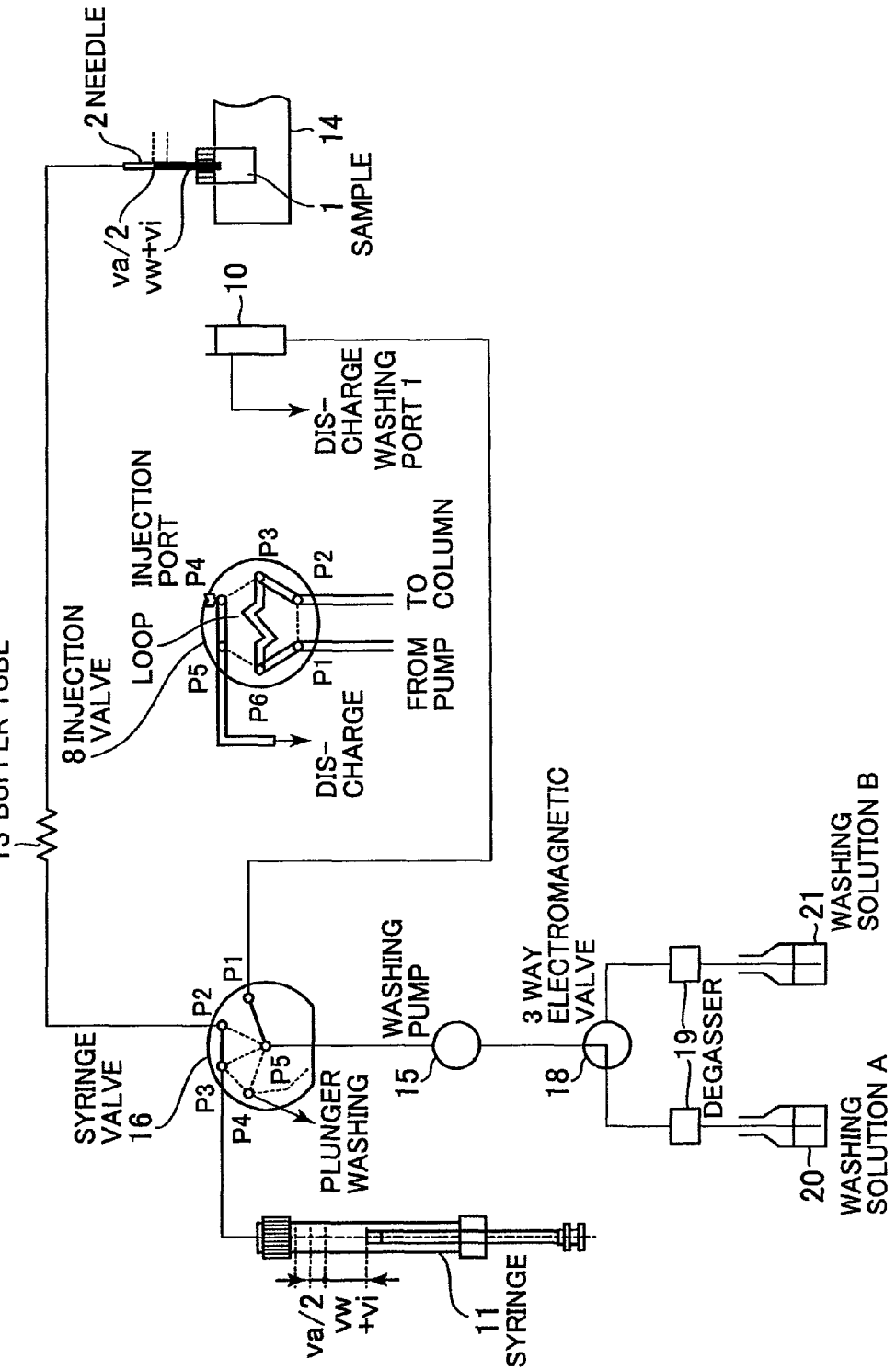
FIG. 20 is a drawing showing a schematic construction and a step for sucking the sample of the liquid chromatograph apparatus according to the third embodiment of the present invention.

FIG. 20 is a drawing to show the step for sucking the sample. In FIG. 20, the syringe 11 sucks the air in volume of the half (va/2) of the air volume during the operation for moving the needle 2 to the sample hold container 1. After the needle 2 is moved in the sample hold container 1, the syringe 11 sucks the sample in volume of vw+vi=waste volume+injection volume.

Figure 21:
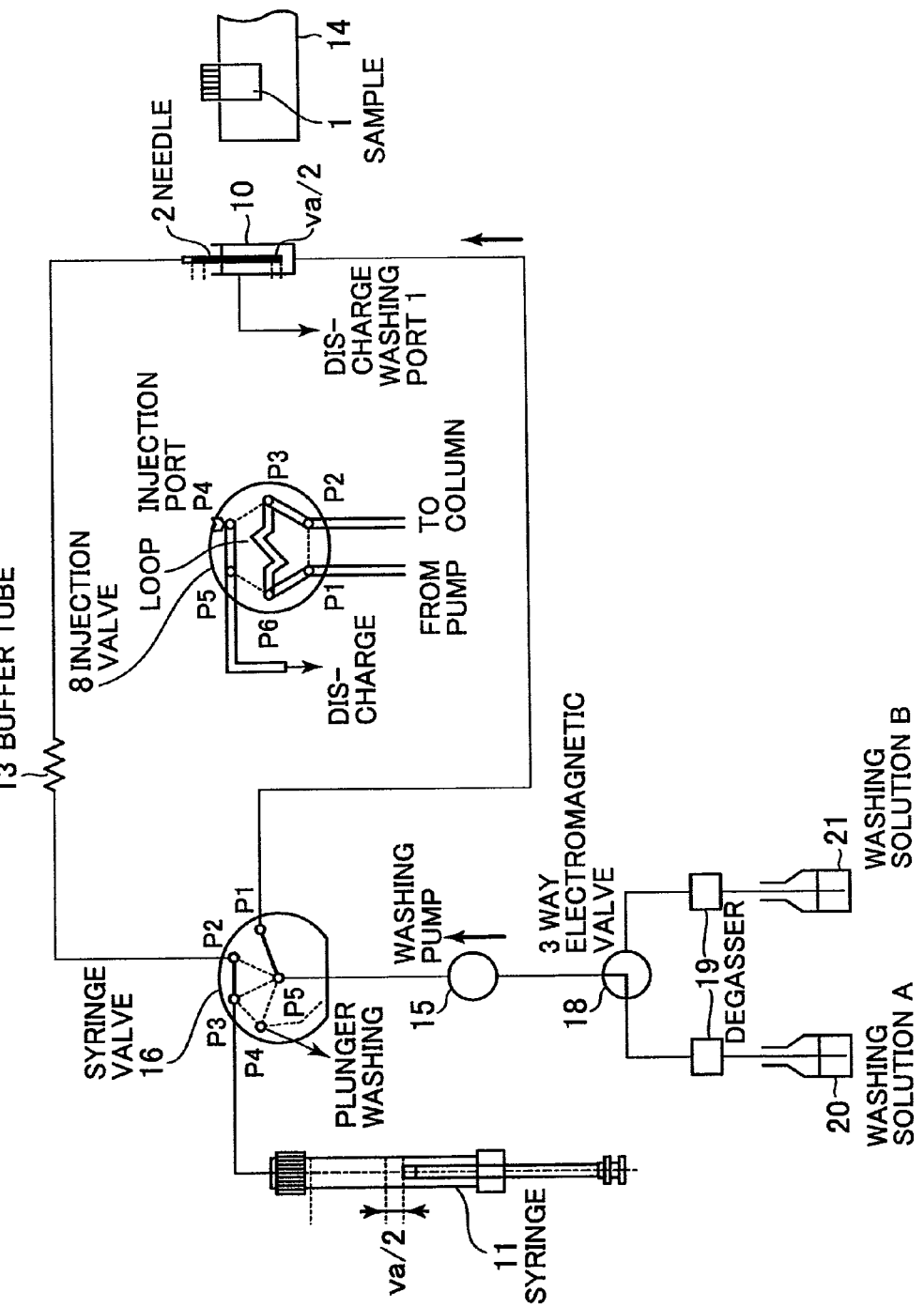
FIG. 21 is a drawing showing a schematic construction and a step for washing the external wall of the needle of the liquid chromatograph apparatus according to the third embodiment of the present invention.

FIG. 21 is a drawing to show the flow passage at the step for washing the external wall of the needle 2 in the washing tank 10 by using the washing solution A in the washing solution tank 20. In FIG. 21, the syringe 11 sucks the air in volume of the half (va/2) of the air volume during the operation for moving the needle 2 to the washing tank 10. After the needle 2 is moved in the washing tank 10, the washing solution A is fed to the washing tank 10 by the washing unit 15 to wash the external wall of the needle 2 (washing operation after the sample sucking operation).

Figure 22:
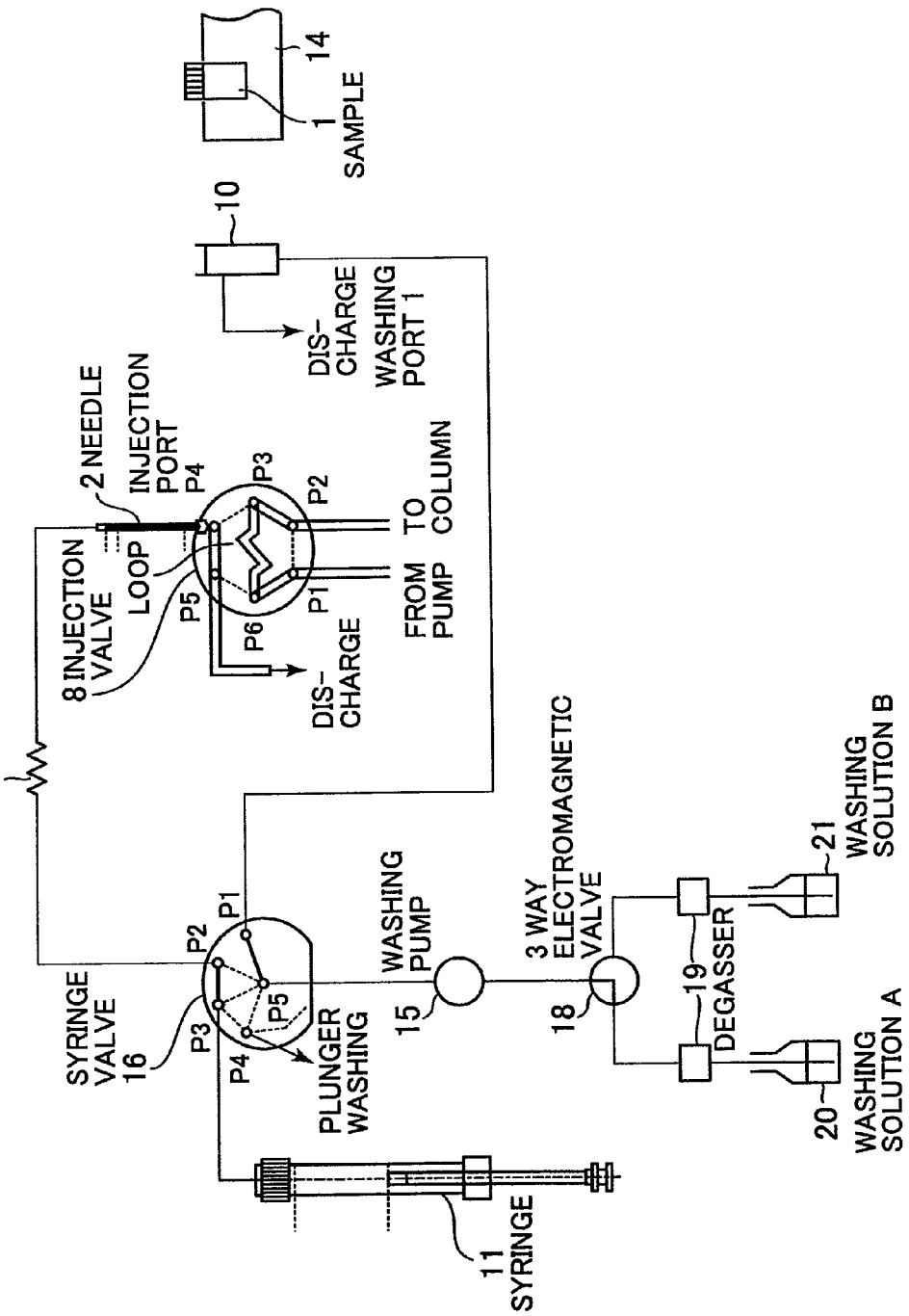
FIG. 22 is a drawing showing a schematic construction and a step for moving the needle for the sample injection port of the liquid chromatograph apparatus according to the third embodiment of the present invention.

FIG. 22 is a drawing to show the flow passage at the moving step for the sample injection port 3 (port P4) of the injection valve 8. In FIG. 22, the needle 2 is moved to the sample injection port 3.

Figure 23:
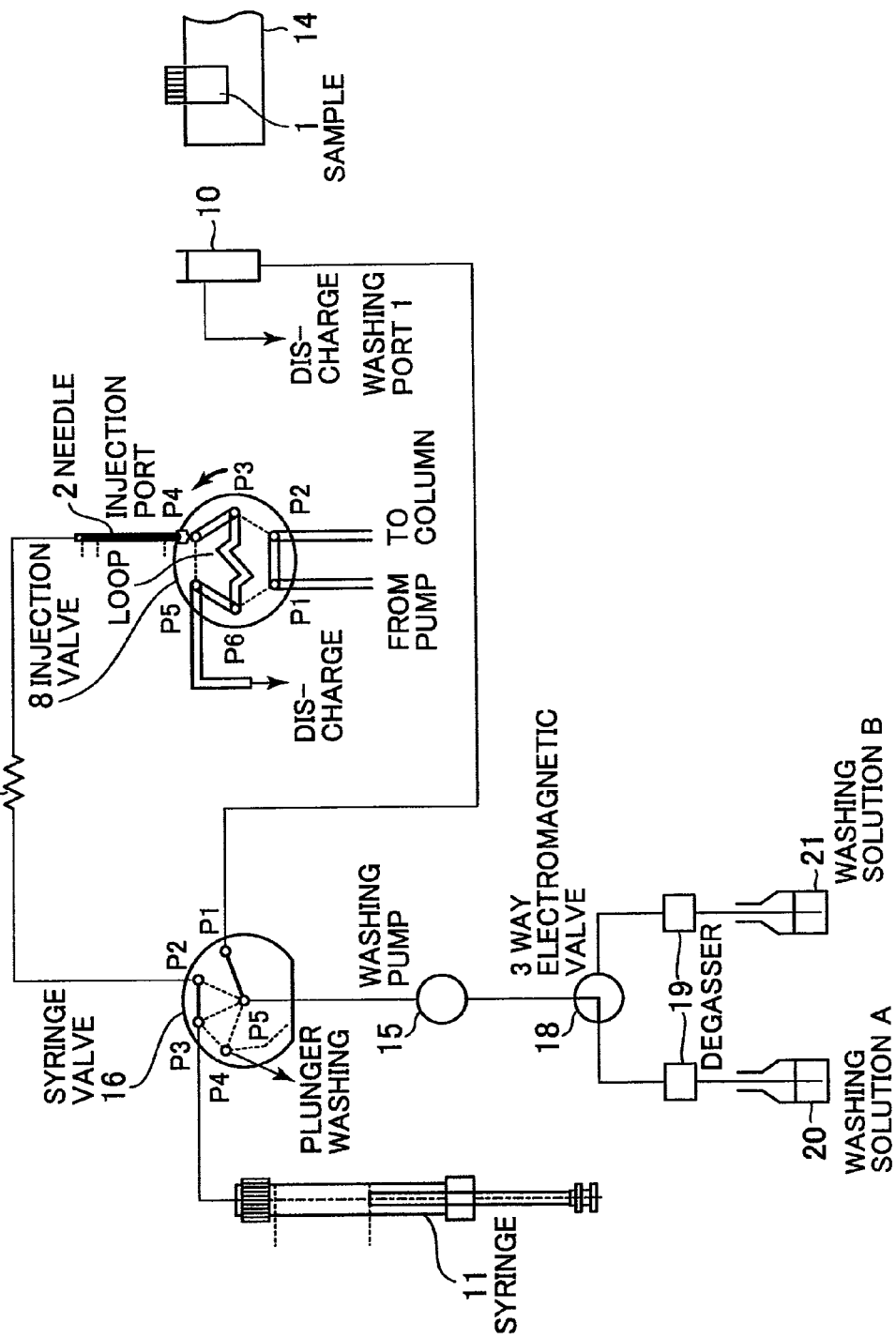
FIG. 23 is a drawing showing a schematic construction and a step for separating the sample storage loop from the mobile phase flow passage and for decreasing the pressure of the sample storage loop of the liquid chromatograph apparatus according to the third embodiment of the present invention.

FIG. 23 is a drawing to show the flow passage at the pressure decreasing step for separating the sample storage loop 5 of the injection valve 8 from the mobile phase flow passage. In FIG. 23, the 6-port 2-position valve 8 is rotated at 60 degrees in counter clockwise direction, so that the sample storage loop 5 under high pressure is separated from the mobile phase flow passage, and the pressure added to the solvent in the sample storage loop 5 is released at the atmospheric pressure through the drain 22.

Figure 24:
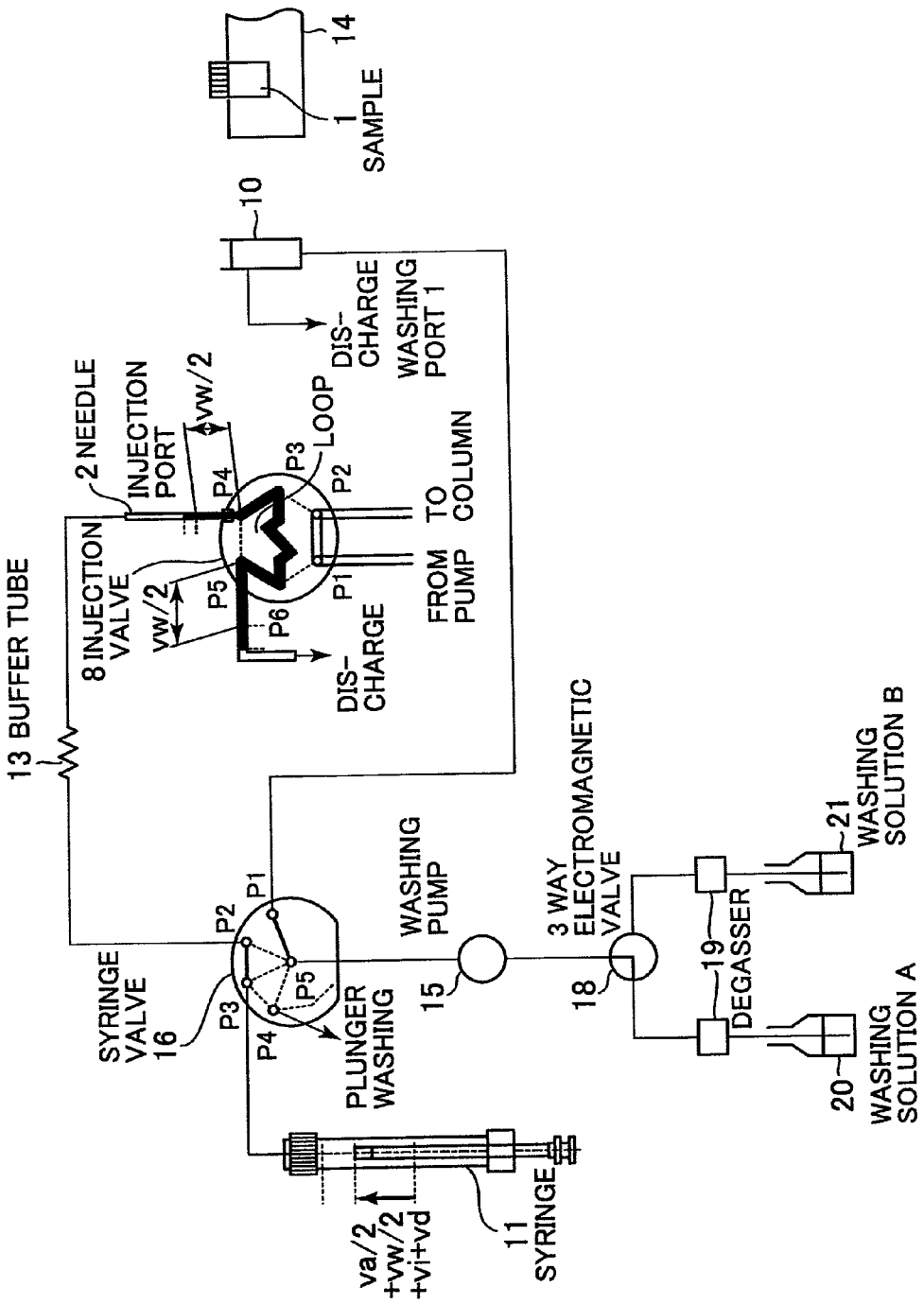
FIG. 24 is a drawing showing a schematic construction and a step for feeding the sample for the sample storage loop of the third embodiment of the present invention.

FIG. 24 is a drawing to show the flow passage at the step for loading the sample. In FIG. 24, the syringe 11 discharges the sample in volume of va/2+vw/2+vi+vd=half of air volume+half of waste volume+injection volume+dead volume, so that the sample is fed into the sample storage loop 5. At this time, all capacity in the sample storage loop 5 is filled with the sample.

Figure 25:
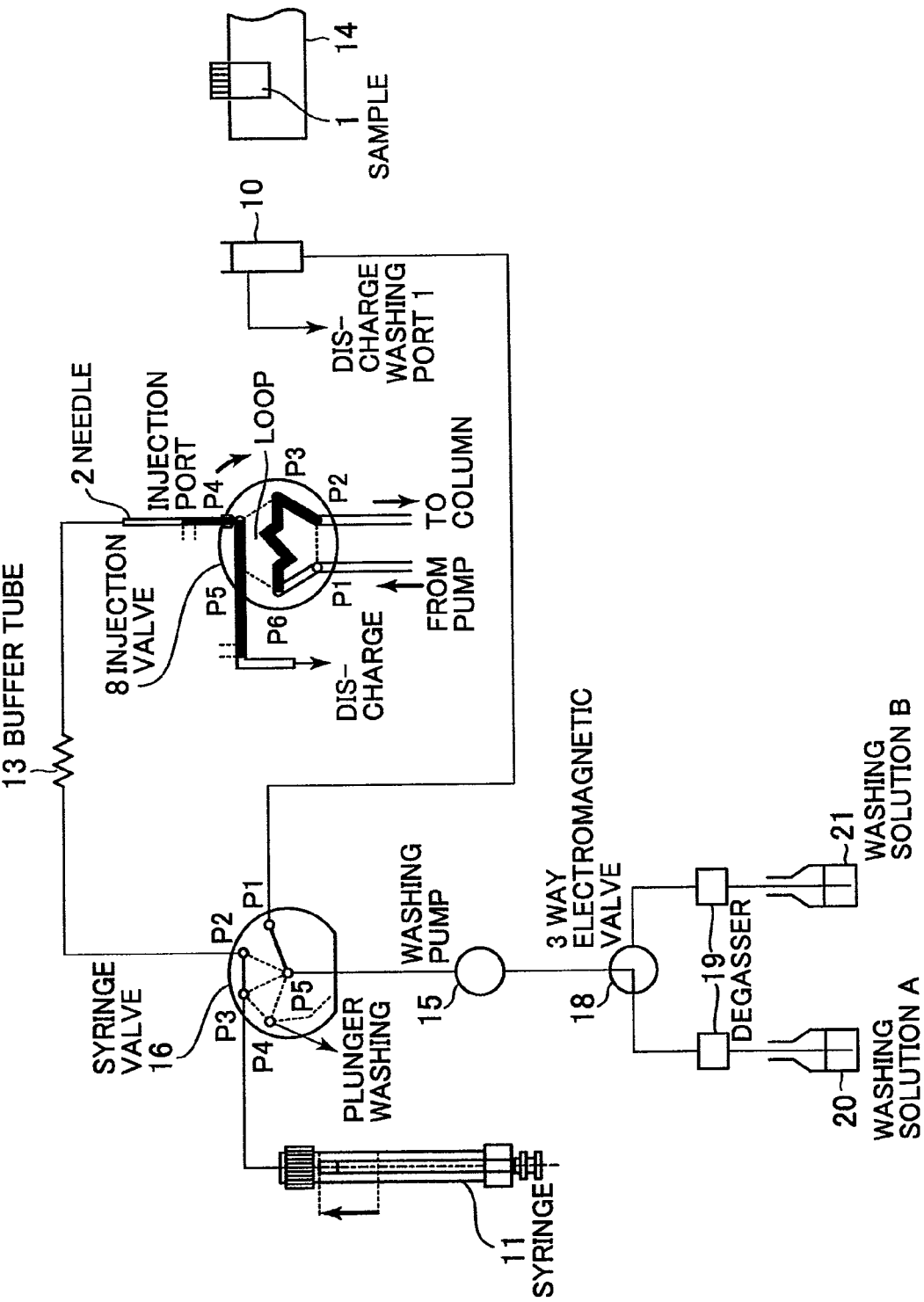
FIG. 25 is a drawing showing a schematic construction and a step for feeding the sample into the mobile phase flow passage from the sample storage loop of the liquid chromatograph apparatus according to the third embodiment of the present invention.

FIG. 25 is a drawing to show the step for discharging the sample. In FIG. 25, the 6-port 2-position valve 8 is rotated at 60 degrees in clockwise direction, so that the sample storage loop 5 is connected to the pump unit 7 and the separation column 6, and the sample is introduced into the mobile phase flow passage. After exchanging the 6-port 2-position valve 8, the syringe 11 is moved to the top dead center.

Herein under, the washing step according to the full loop system is equal to the step as shown in FIGS. 1 to 11.

The third embodiment of the present invention can also realize the liquid chromatograph apparatus and the automatic sample introducing apparatus used for the liquid chromatograph apparatus capable for improving the basic performance and for executing the processes at high speed and high reliability, as same as the first embodiment.

Figure 26:
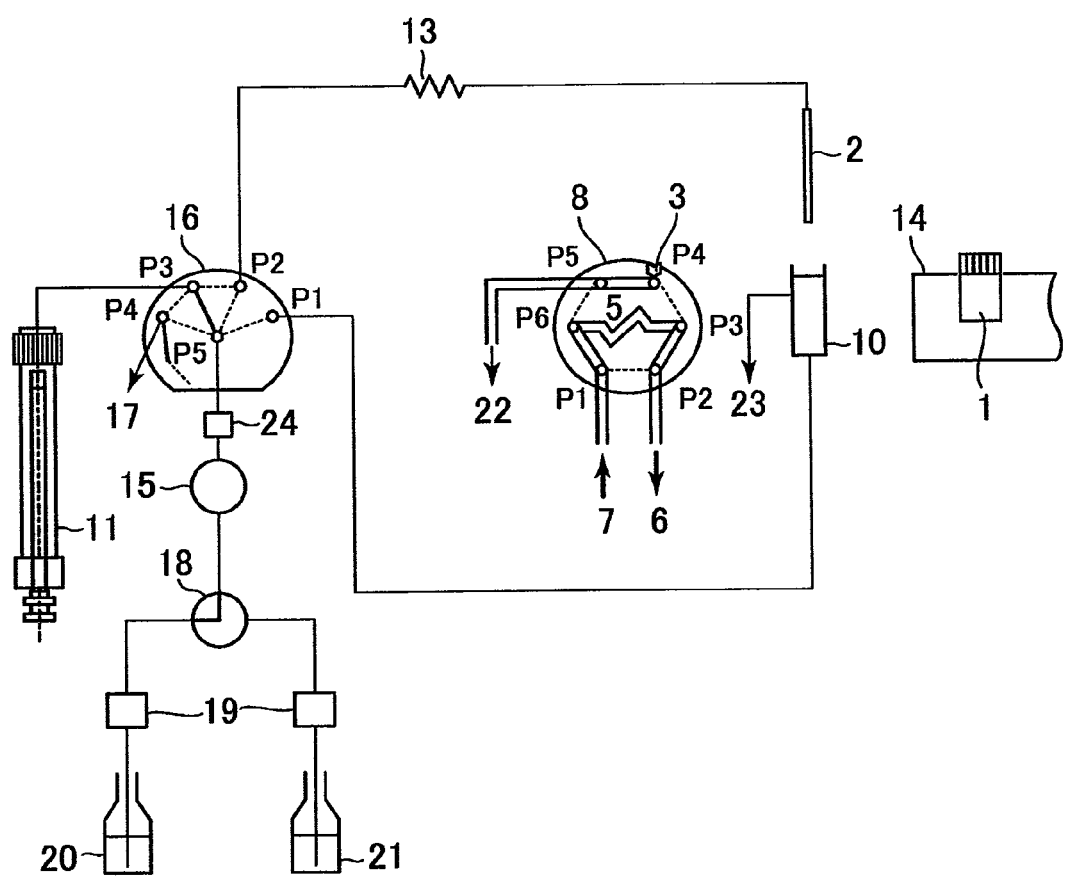
FIG. 26 is a drawing showing a schematic construction the liquid chromatograph apparatus according to the fourth embodiment of the present invention.

FIG. 26 explains the detail of the sample injection step of the fourth embodiment according to the present invention.

The fourth embodiment is an example of a liquid chromatograph apparatus using a loop injection system automatic sample introduction apparatus, as same as the first embodiment.

The different point between the fourth embodiment and the first embodiment shown in FIG. 1 is that the pressure sensor 24 is set between the washing unit 15 and the port P5 of the 5-port 4-position valve 16 in the fourth embodiment. Other constructions of the first and the forth embodiments are equal with each other.

In the washing step of the fourth embodiment of the present invention, the liquid feeding condition of the washing unit 15 can be confirmed by the operation control unit 50 (FIG. 43) for monitoring the pressure value of a pressure sensor 24. Further, since the upper limit and lower limit of the pressure are set, the apparatus can judge that the needle 2 or buffer pipe 13 is blocked, and the apparatus can judge that the liquid leaks at the downstream from the washing unit 15.

Further, the pressure sensor 24 may be set between the port P2 of the 5-port 4-position valve 16 and the buffer pipe 13. In this case, since the pressure value is monitored at the sample suction step, it can be judged whether the sample is sucked correctly or not. The judgment is executed by the operation control unit 50.

Next, the sample injection step of the fifth embodiment of the present invention will be described with reference to FIGS. 27 to 42. The fifth embodiment is an example of a liquid chromatograph apparatus using a loop injection system automatic sample introduction apparatus, as same as the first embodiment.

Figure 27:
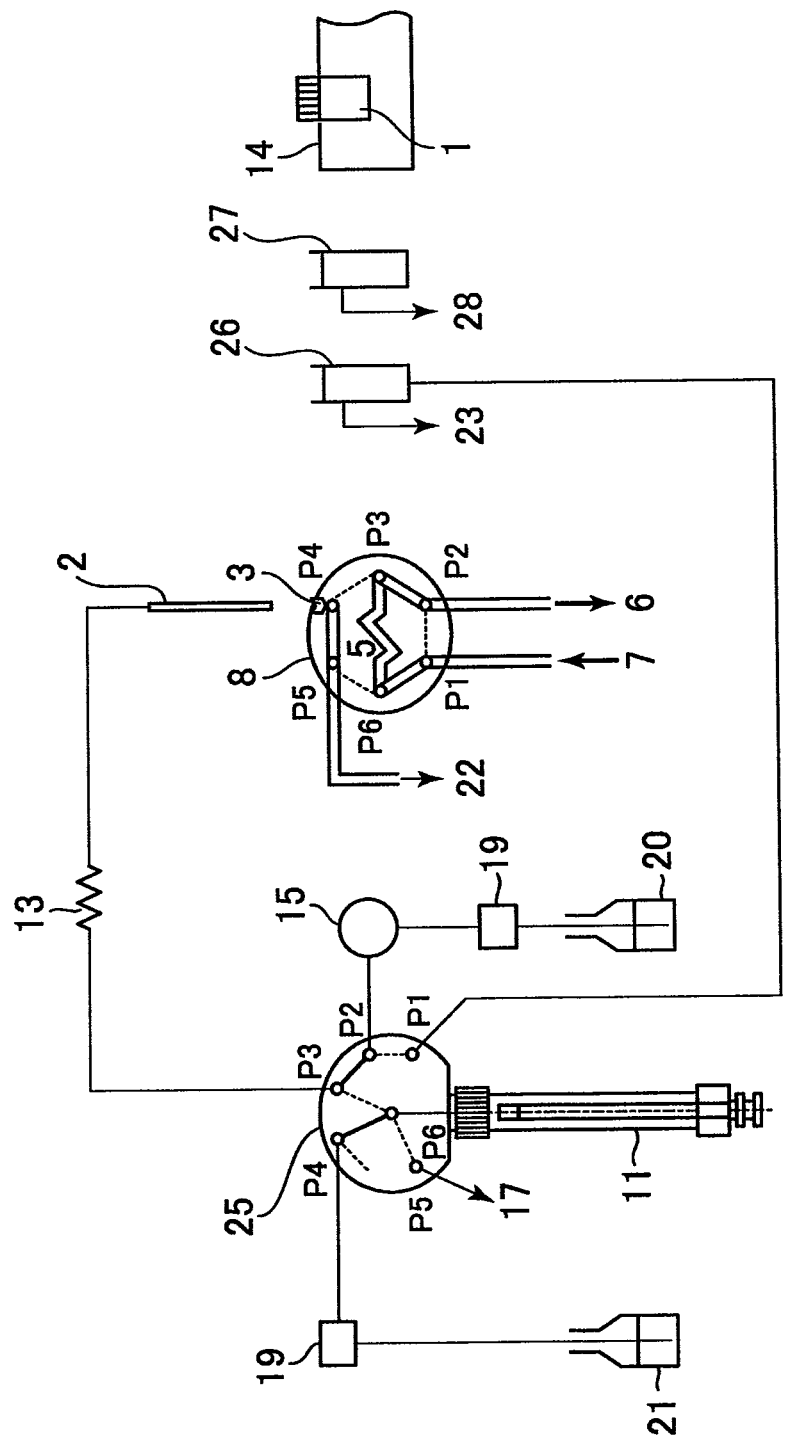
FIG. 27 is a drawing showing a schematic construction and an idling condition of a liquid chromatograph apparatus according to the fifth embodiment of the present invention.

In FIG. 27, the sample hold container 1 is set on the sample rack 14. The needle 2 can freely move between the sample hold container 1, washing tank 10, and the sample injection port 3. In the 6-port 2-position valve 8, the pump unit 7 is connected to the port P1, the column 6 being connected to the port P2, the sample injection port 3 being connected to the port P4, the drain 23 being connected to the port P5, the sample storage loop 5 being connected between the port P3 and the port P6. The 6-port 2-position valve 8 is rotated at 60 degrees, so that the 6-port 2 position valve 8 sets the two conditions of the discharge position to communicate the port P1-P6, P4-P5, and P2-P3, and the load position to communicate the port P1-P2, P3-P4, and P5-P6.

In the 6-port 3-position valve 25, the washing tank 26 is connected to the port P1, the washing unit 15 being connected to the port P2, the buffer pipe 13 being connected to the port P3, the washing solution bottle 21 being connected to the port P4 through the degasser unit 19, the plunger washing flow passage 17 being connected to the port P5, the syringe 11, which is the sample accounting means, being connected to the common port P6.

The plunger washing flow passage 17 communicates the pump unit 7 (omitted in FIG. 27), being capable for washing the salt, which is to be deposited on the surface of the plunger of the pump unit 7, in the mobile phase from the automatic sample introducing apparatus. The 6-port 3-position valve 25 is rotated at 45 degrees or 90 degrees, so that the valve 25 can set at the 3 positions of (1) the port P1-P2 and P3-P6 communicated with each other, (2) the port P2-P3 and P4-P6 communicated with each other, and (3) the port P5-P6 communicated with each other.

When the 6-port 3-position valve 25 is set at the (1) the port P1-P2 and P3-P6 communicated with each other, the needle 2 is connected to the syringe 11, which is a sample accounting means, through the buffer pipe 13, and the liquid is sucked and discharged by operating the syringe 11 moving up and down.

The washing solution bottle 20 is connected to the washing unit 15 through the degasser unit 19. In the fifth embodiment of the present invention, a washing tank 27 is newly installed.

Next, the sample injection step of the fifth embodiment of the present invention will be described with reference to FIGS. 27 to 42.

The loop injection system in the fifth embodiment of the present invention is the all volume injection system that all volume of the sample sucked form the needle 2 are fed into the sample storage loop 5 to be reached to the column 6. Therefore, the terms equal to the terms used in the second embodiment are used.

Further, it can be selected in an automatic sample introducing apparatus whether or not the air volumes va are inserted at the front side and the rear side of the sample. The fifth embodiment of the present invention is the example of va=0 (air volume is not inserted at the front side and the rear side of the sample).

FIG. 27 is a drawing to show the flow passage of the idle condition after the initializing operation of the automatic sample introduction apparatus. In FIG. 27, the mobile phase flows to the separation column 6 from the pump unit 7 through the sample storage loop 5 of the 6-port 2-position valve 8. The washing solution bottle 20 is connected to the buffer pipe 13 through the degassing unit (degasser) 19, the washing unit 15, and the ports P2 and P3 of the 6-port 3-position valve 25. Further, syringe 11 is connected to the washing solution bottle 21 through the ports P4 and P6 of the 6-port 3-position valve 25 and the degassing unit 19. Further, the needle 2 is positioned above the sample injection port 3.

Figure 28:
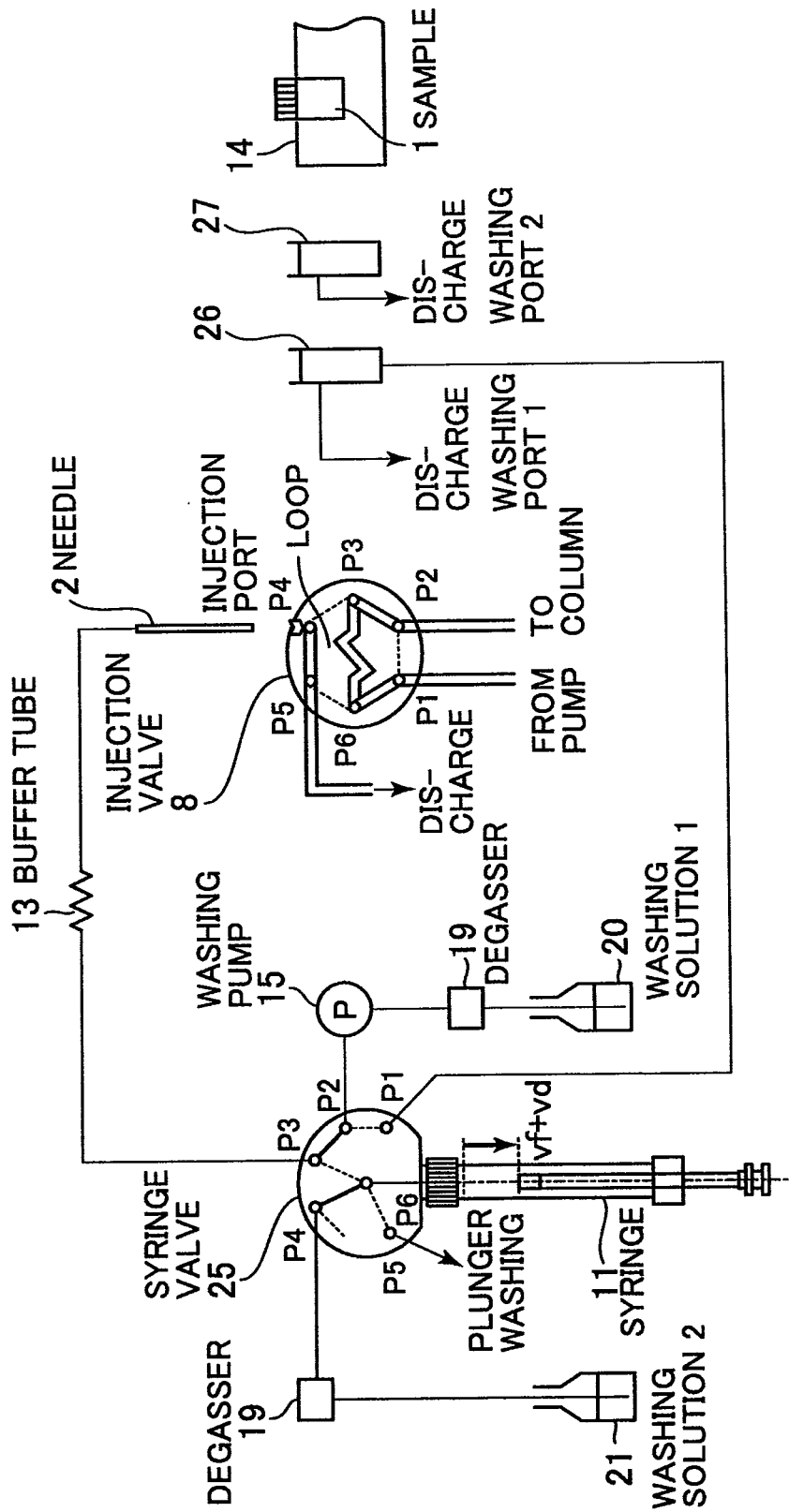
FIG. 28 is a drawing showing a schematic construction and a step for sucking the washing solution of the syringe of a liquid chromatograph apparatus according to the fifth embodiment of the present invention.

FIG. 28 is a drawing to show the flow passage at the step of sucking the washing solution A. In FIG. 28, the syringe 11 sucks the washing solution A in volume of vf+vd=feed volume+dead volume. Further, the washing step of the external wall of the needle 2 before the sample sucking operation is not described in the fifth embodiment, the external wall of the needle 2 can be washed before the sample sucking operation by rotating the 6-port 3-position valve 25 at 45 degrees in the clockwise direction to move the needle 2 for the washing tank 26 to feed the washing solution A by using the washing unit 15 before sample sucking operation (washing before sample sucking operation).

Figure 29:
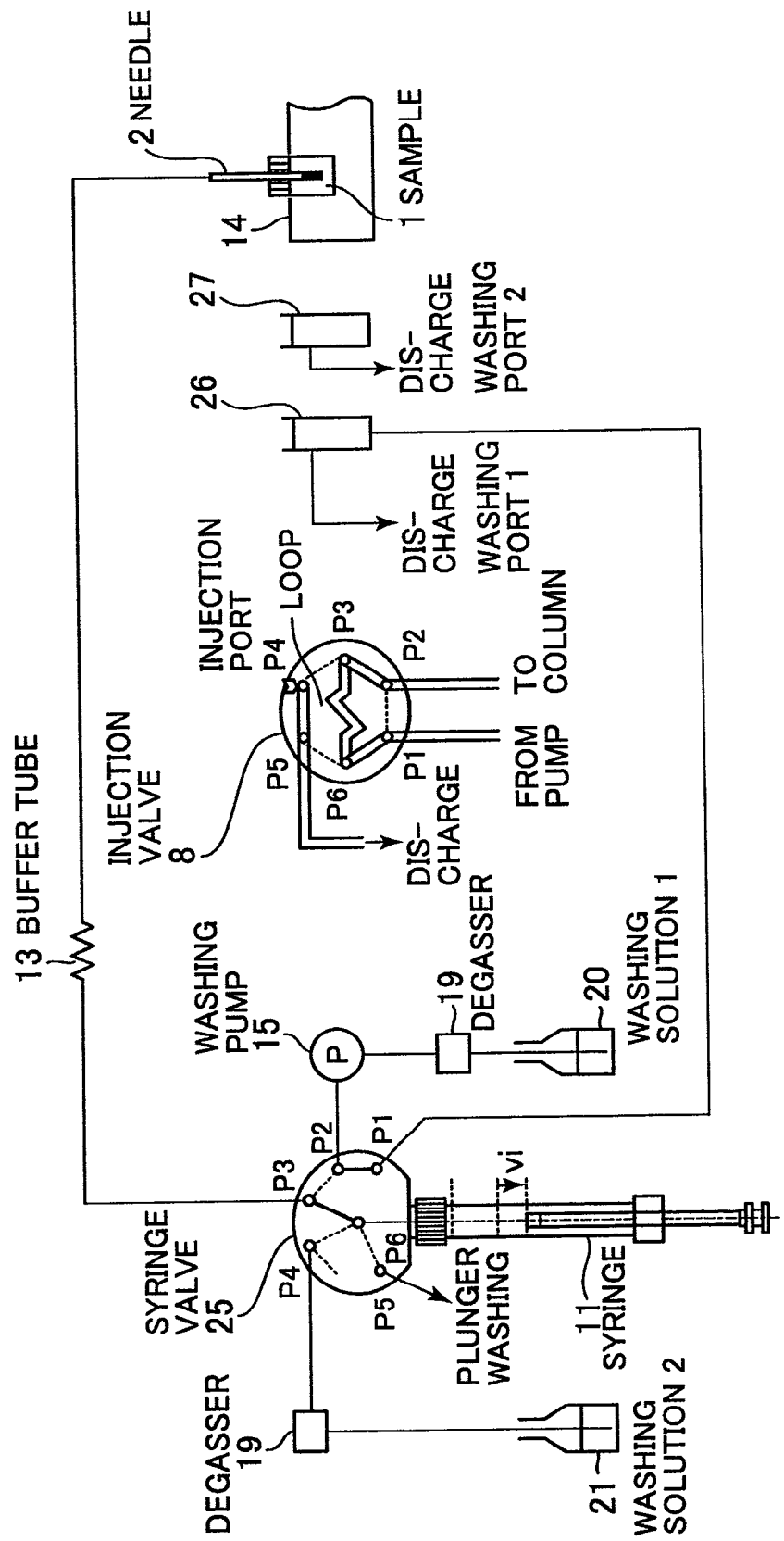
FIG. 29 is a drawing showing a schematic construction and a step for sucking the sample of a liquid chromatograph apparatus according to the fifth embodiment of the present invention.

FIG. 29 is a drawing to show the flow passage of the sample sucking operation. In FIG. 29, the 6-port 3-position valve 25 is rotated at 45 degrees in the clockwise direction, so that the position of the valve 25 is exchanged into the position (1) to communicate the ports P1-P2 and P3-P6 respectively. After the needle 2 is moved in the sample hold container 1, the syringe 11 sucks the sample in volume of the injection volume (vi).

Figure 30:
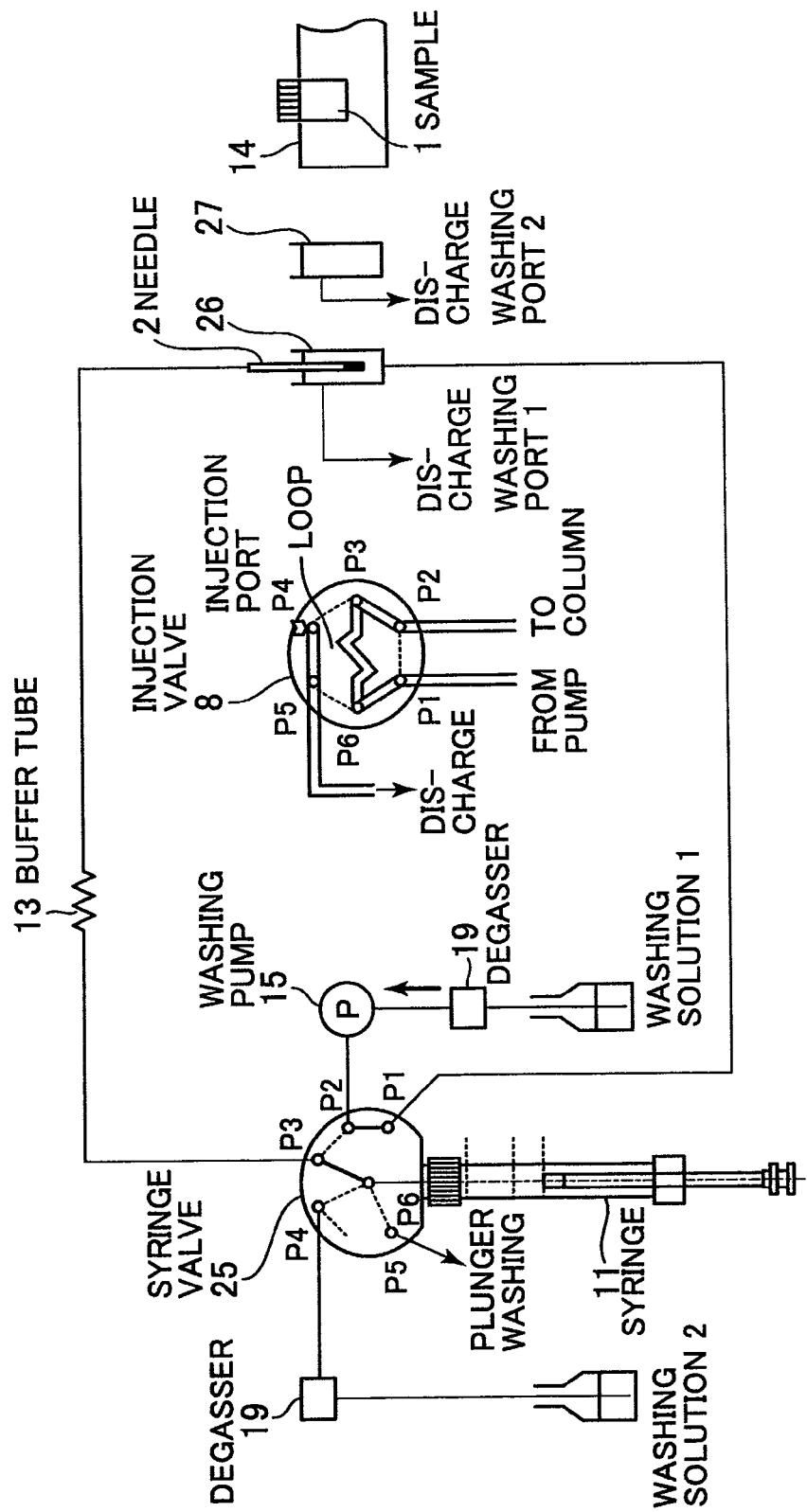
FIG. 30 is a drawing showing a schematic construction and a step for washing the external wall of the needle of a liquid chromatograph apparatus according to the fifth embodiment of the present invention.

FIG. 30 is a drawing to show the passage of the step for washing the external wall of the needle 2 by using the washing solution A in the washing tank 26. In FIG. 30, after the needle 2 is moved to the washing tank 26, the washing solution A is fed into the washing tank 26 by the washing unit 15, and the external wall of the needle 2 is washed (washing after the sample sucking operation).

Figure 31:
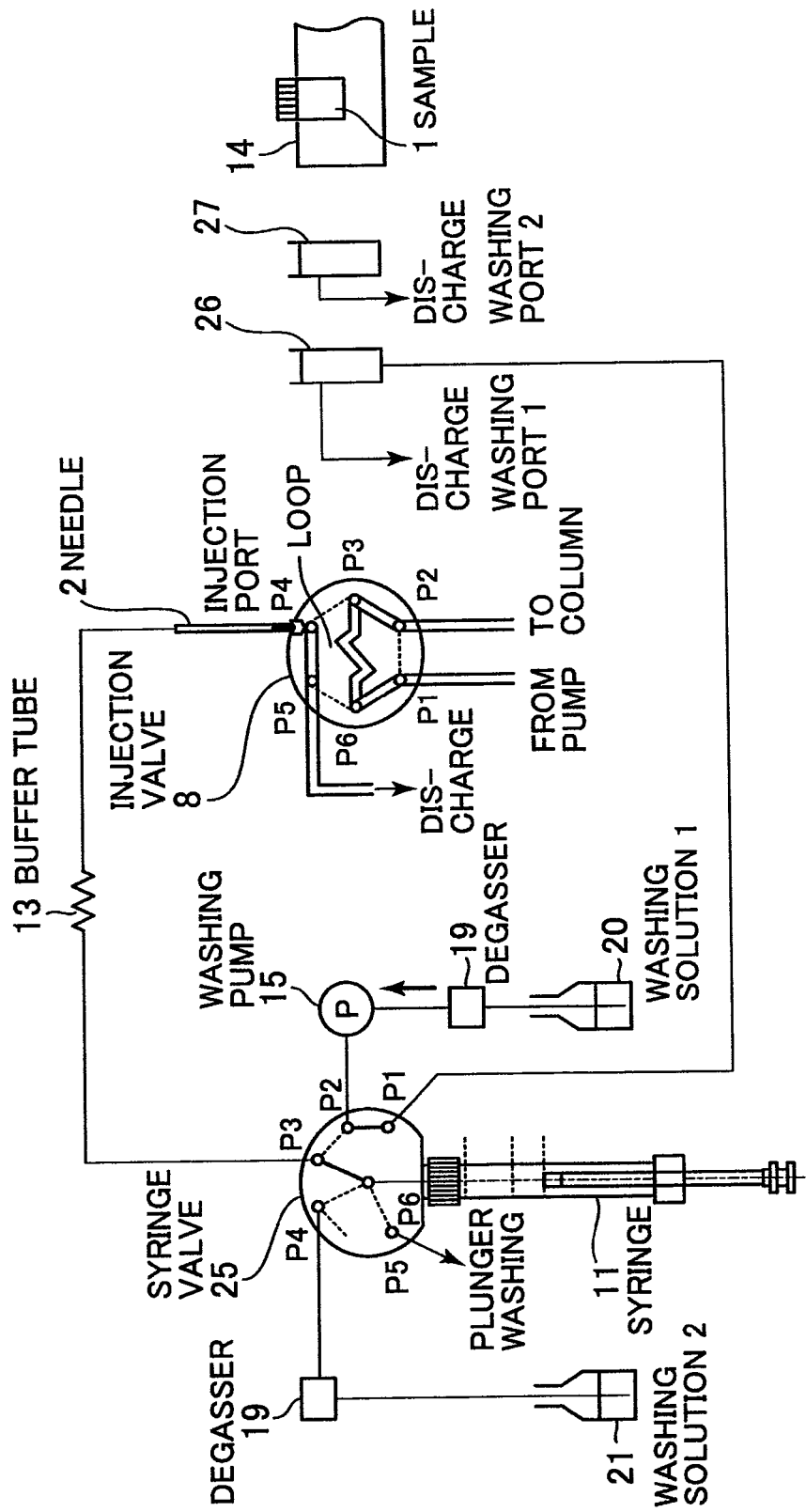
FIG. 31 is a drawing showing a schematic construction and a step for moving the needle for the sample injection port of a liquid chromatograph apparatus according to the fifth embodiment of the present invention.

FIG. 31 is a drawing to show the flow passage of the step for exchange the position into the sample injection port 3 (port P4) of the injection valve 8. In FIG. 31, the needle 2 is moved to the sample injection port 3.

Figure 32:
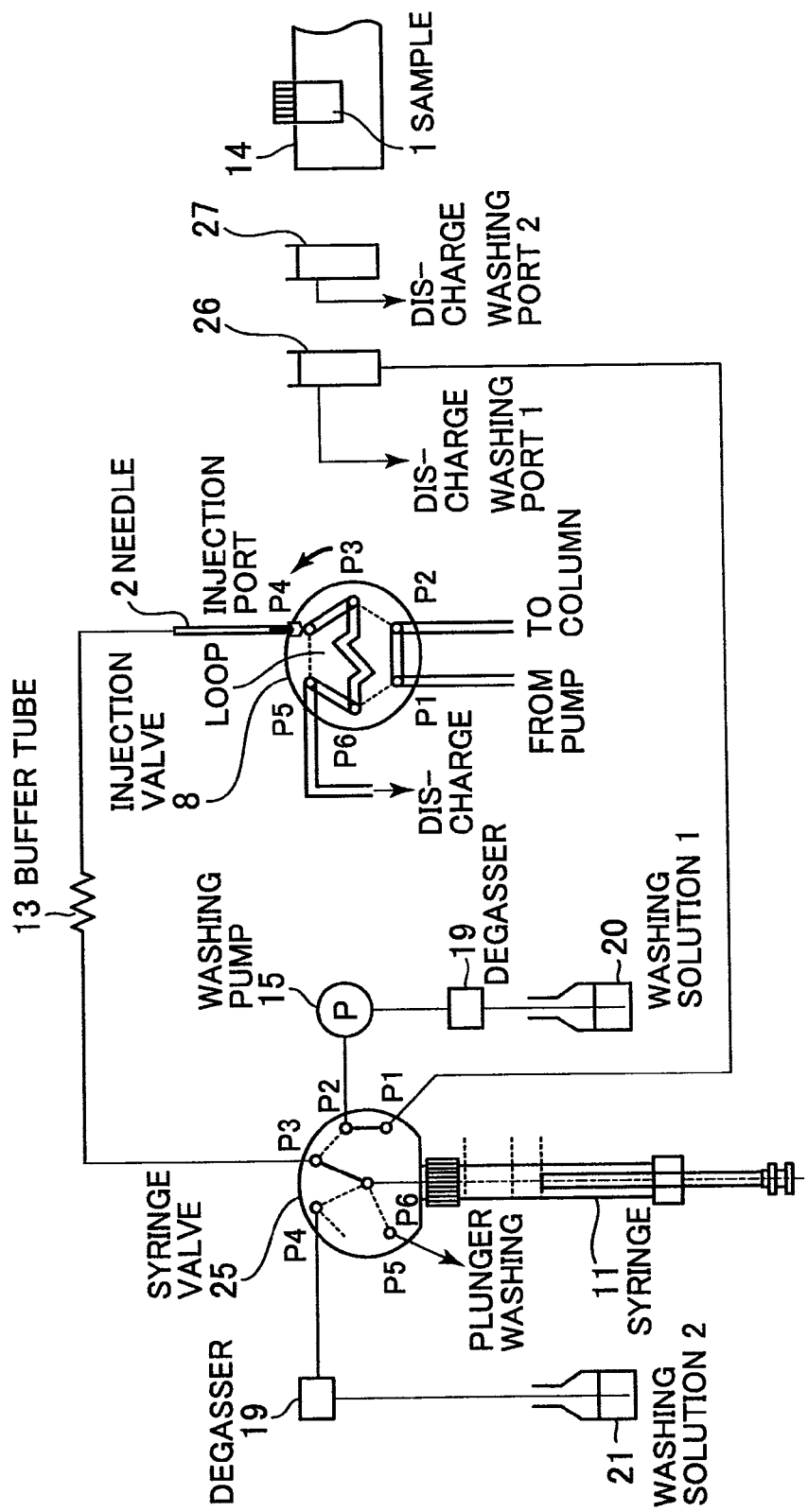
FIG. 32 is a drawing showing a schematic construction and a step for separating the sample storage loop from the mobile flow passage and for decreasing the pressure in the sample storage loop of a liquid chromatograph apparatus according to the fifth embodiment of the present invention.

FIG. 32 is a drawing to show the flow passage of the pressure decreasing step for separating the sample storage loop 5 of the injection valve 8 from the mobile phase flow passage. In FIG. 32, the 6-port 2-position valve 8 is rotated at 60 degrees in the counterclockwise direction, so that the sample storage loop 5 under high pressure is separated from the mobile phase flow passage, and the pressure loaded to the solvent in the sample storage loop 5 is released at atmosphere pressure through the drain 22.

Figure 33:
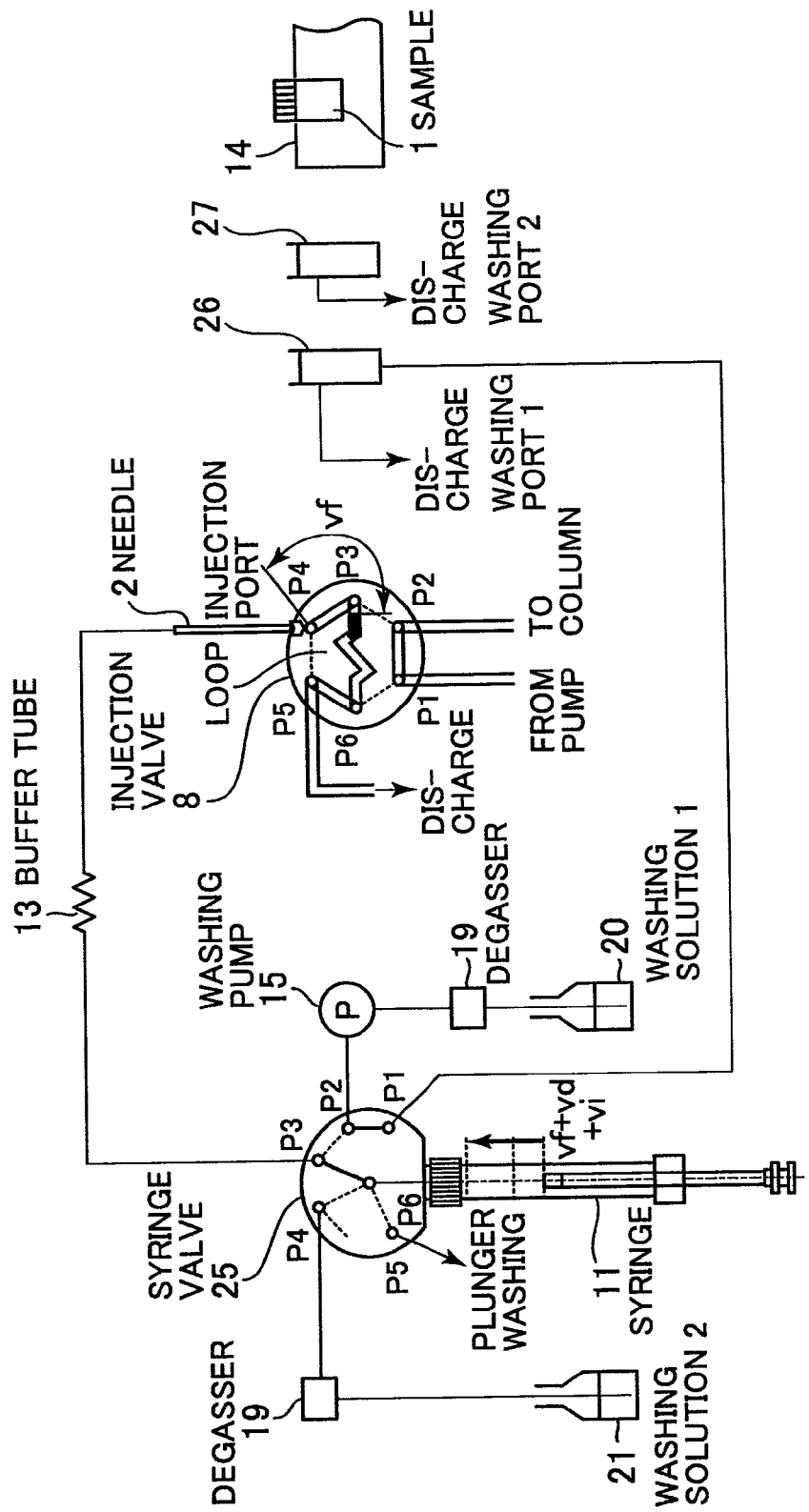
FIG. 33 is a drawing showing a schematic construction and a step for feeding the sample to the sample storage loop of a liquid chromatograph apparatus according to the fifth embodiment of the present invention.

FIG. 33 is a drawing to show the passage of the step for loading the sample. In FIG. 33, the syringe 11 discharges the sample in volume of vf+vi+vd=feed volume+injection volume+dead volume to feed the sample into the sample storage loop 5 of the injection valve 8. All volume (vi) of the sample sucked from the needle 2 are held in the sample storage loop 5.

Figure 34:
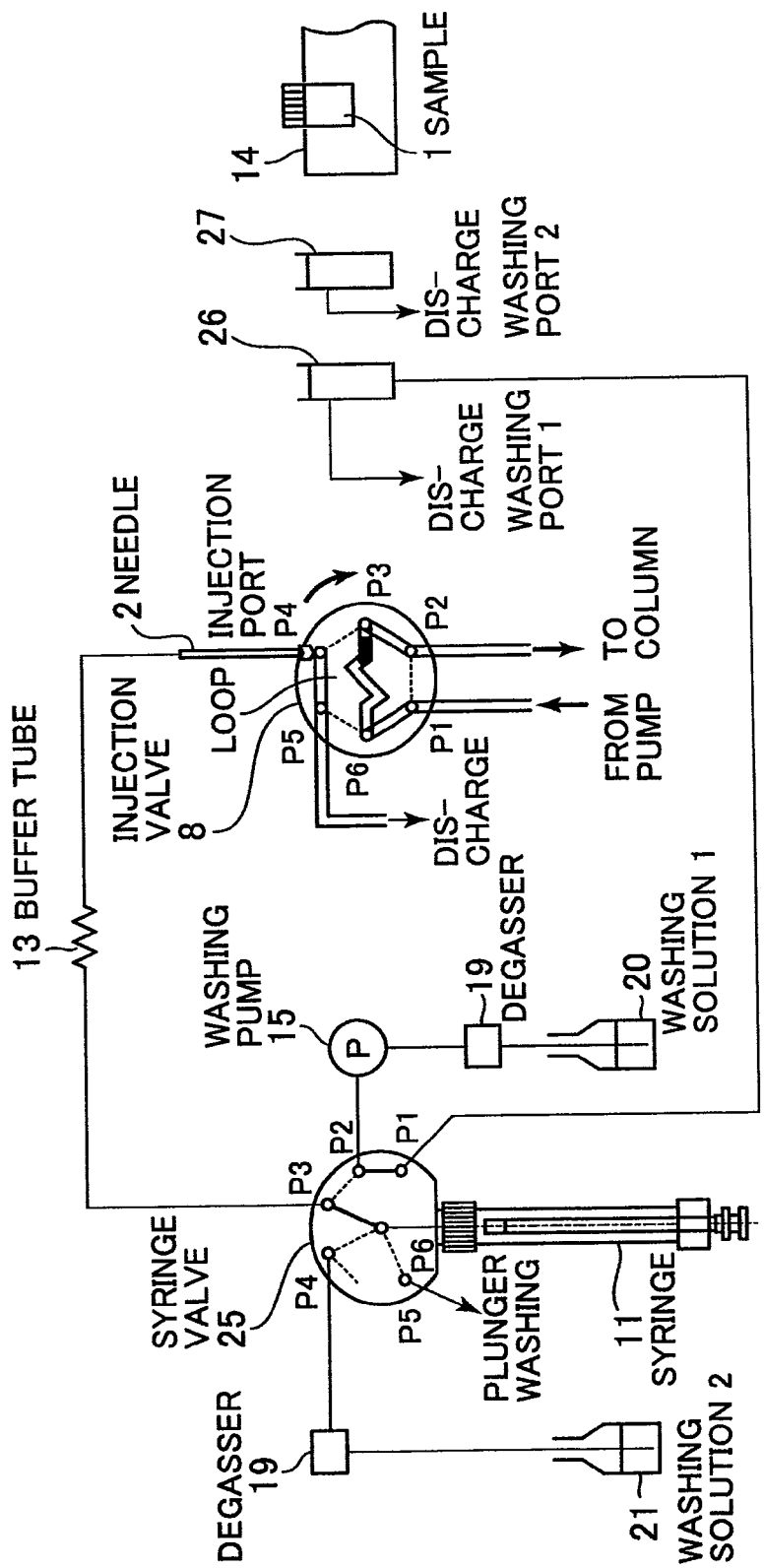
FIG. 34 is a drawing showing a schematic construction and a step for feeding the sample to the mobile phase flow passage from the sample storage loop of a liquid chromatograph apparatus according to the fifth embodiment of the present invention.
Figure 35:
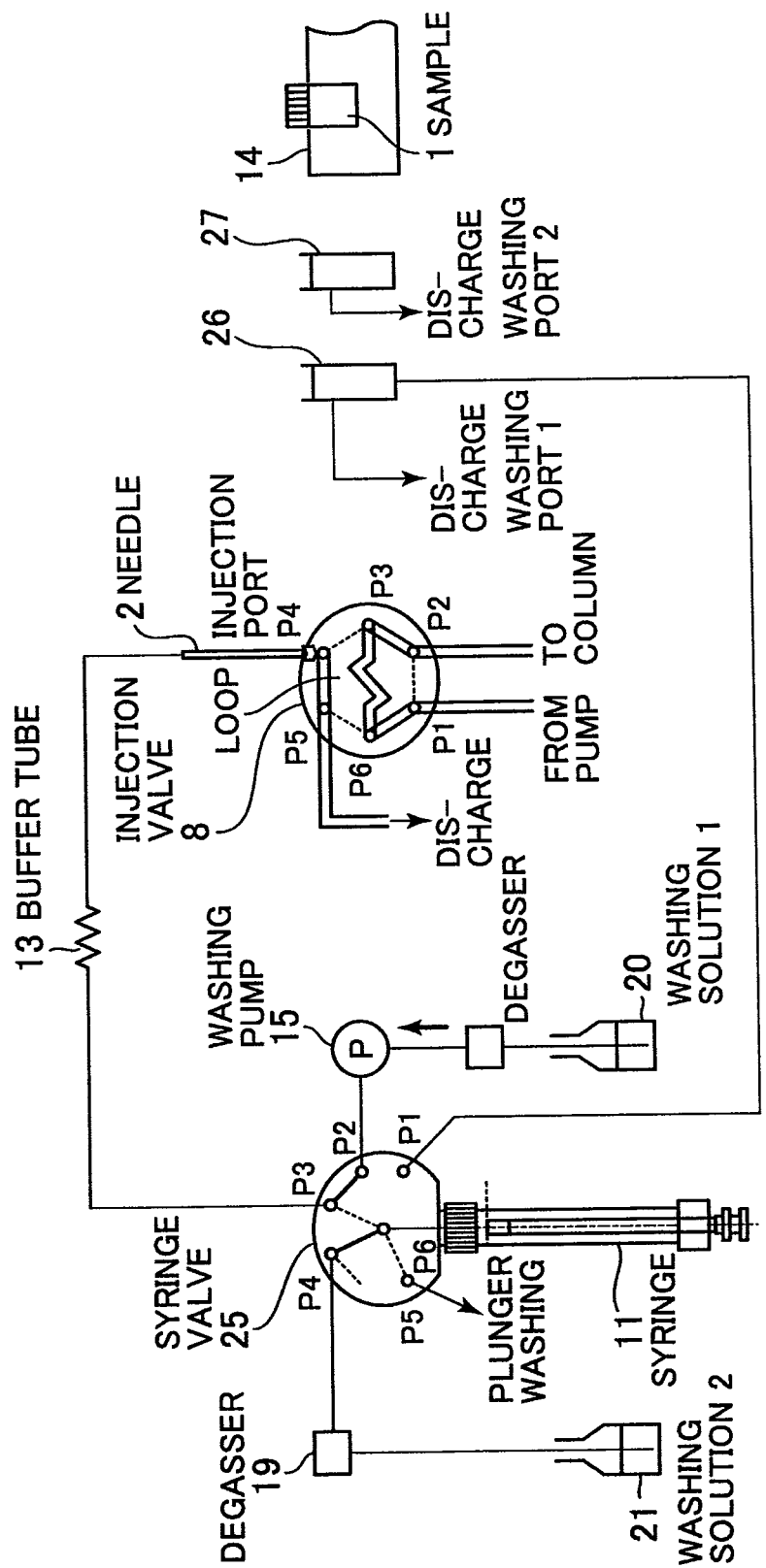
FIG. 35 is a drawing showing a schematic construction and a step for washing the inner wall of the needle of a liquid chromatograph apparatus according to the fifth embodiment of the present invention.

FIG. 34 is a drawing to show the passage of the step for discharging the sample. In FIG. 34, the 6-port 2-position valve 8 is rotated at 45 degrees in the counterclockwise direction, so that the position is exchanged into the position (2) to communicate the ports P2-P3 and the port P4-P6, and the washing solution A in the washing solution bottle 20 is fed by the washing unit 15. Further. The passages of the buffer pipe 13, the needle 2, the sample injection port 3, and the 6-port 2-position valve 8 are washed by the washing solution A, and the washing solution A is discharged to the drain 22.

Figure 36:
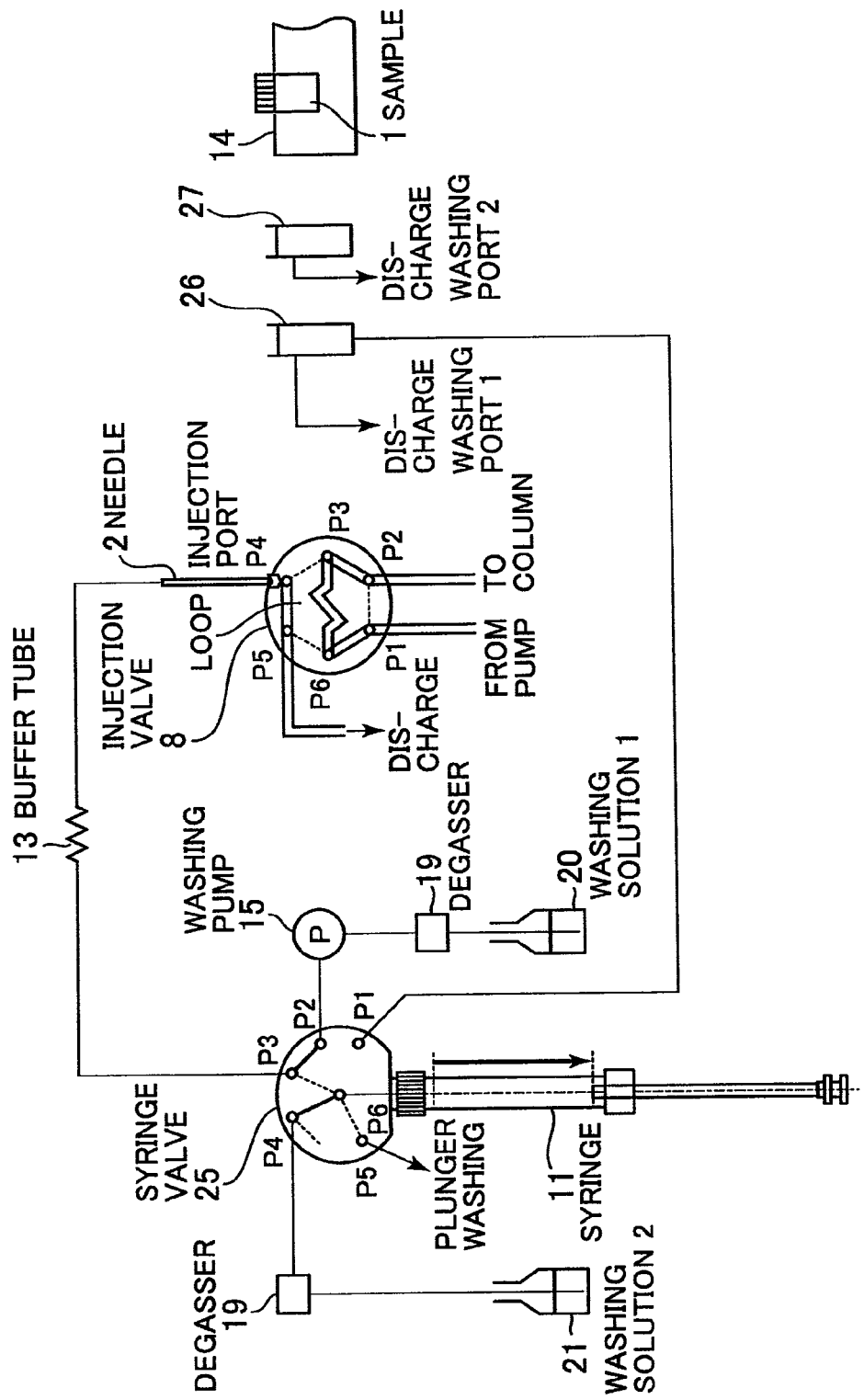
FIG. 36 is a drawing showing a schematic construction and a step for washing the inner wall of the needle of a liquid chromatograph apparatus according to the fifth embodiment of the present invention.
Figure 37:
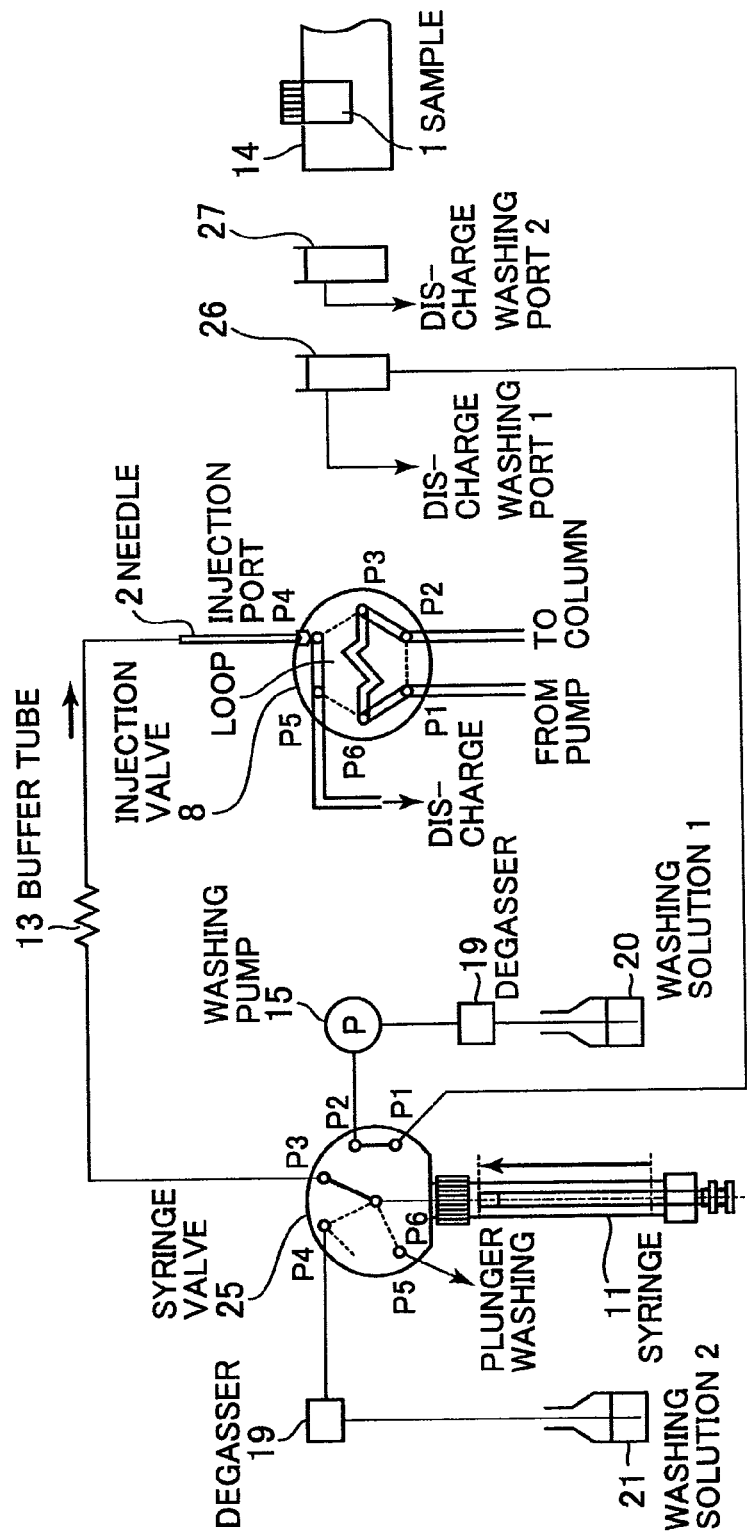
FIG. 37 is a drawing showing a schematic construction and a step for washing the inner wall of the needle of a liquid chromatograph apparatus according to the fifth embodiment of the present invention.

FIGS. 36 and 37 are drawings to show the passage of the step for washing the inner wall of the needle 2 by using the washing solution B in the washing solution bottle 21. In FIG. 36, the syringe 11 is moved downwardly to suck the washing solution B from the washing solution bottle 21.

In FIG. 37, the 6-port 3-position valve 25 is rotated at 45 degrees in the clockwise direction to exchange the position into the position (1) to communicate the ports P1-P2 and P3-P6 respectively. The syringe 11 is moved upwardly, and the passages in the buffer pipe 13, the needle 2, the sample injection port 3, and the 6-port 2-position valve 8 are washed by the washing solution B, and the washing solution b is discharged to the drain 22.

Figure 38:
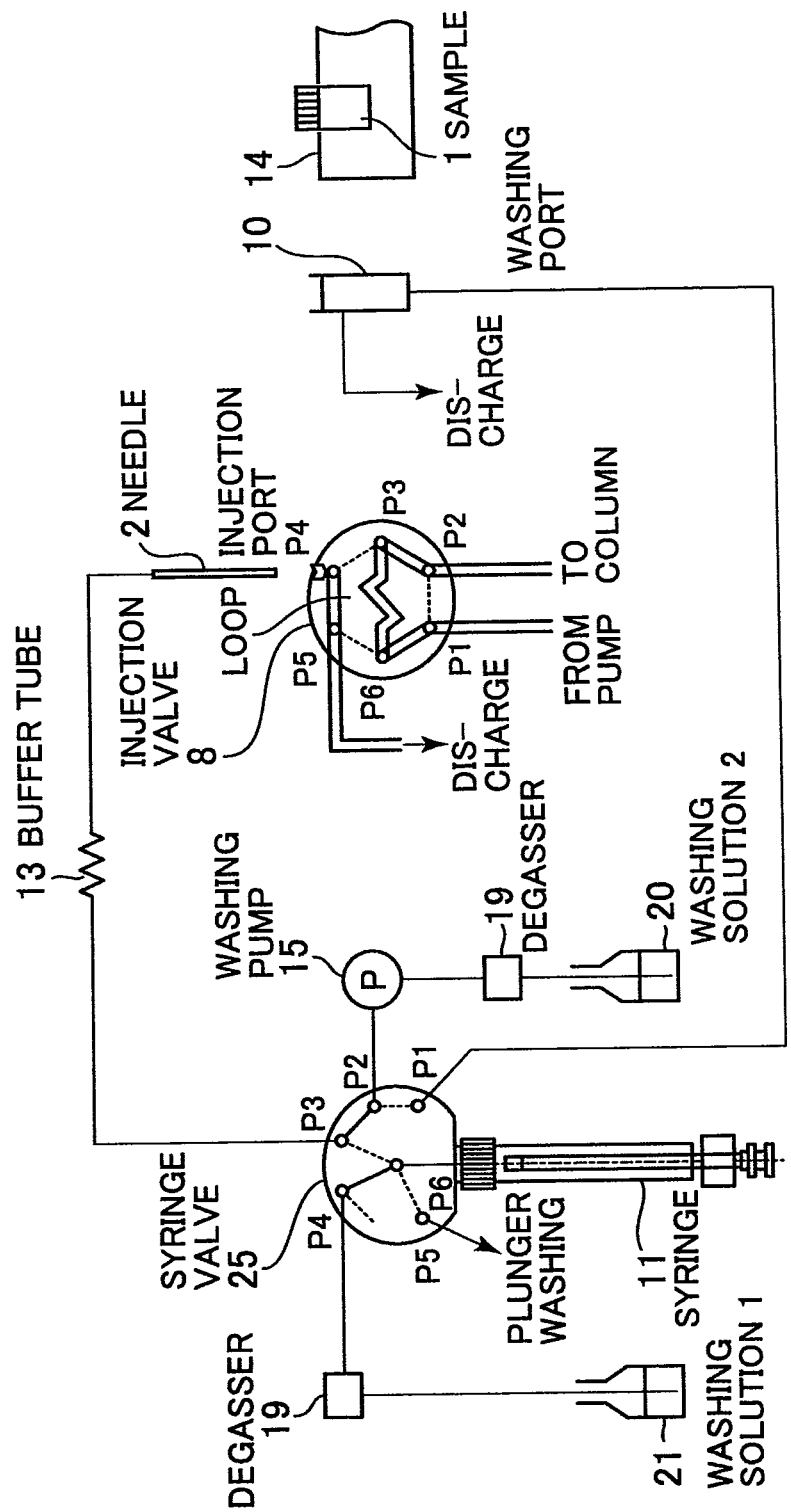
FIG. 38 is a drawing showing a schematic construction and an idling condition of a liquid chromatograph apparatus according to the fifth embodiment of the present invention.

FIG. 38 is a drawing to show the passage of the idling condition shifted after the washing operation. In FIG. 38, the 6-port 3-position valve 25 is rotated at 45 degrees in the counterclockwise to exchange the position to the position (2) to communicate the ports P2-P3 and P4-P6. Further, the needle 2 is moved above the sample injection port 3.

Figure 39:
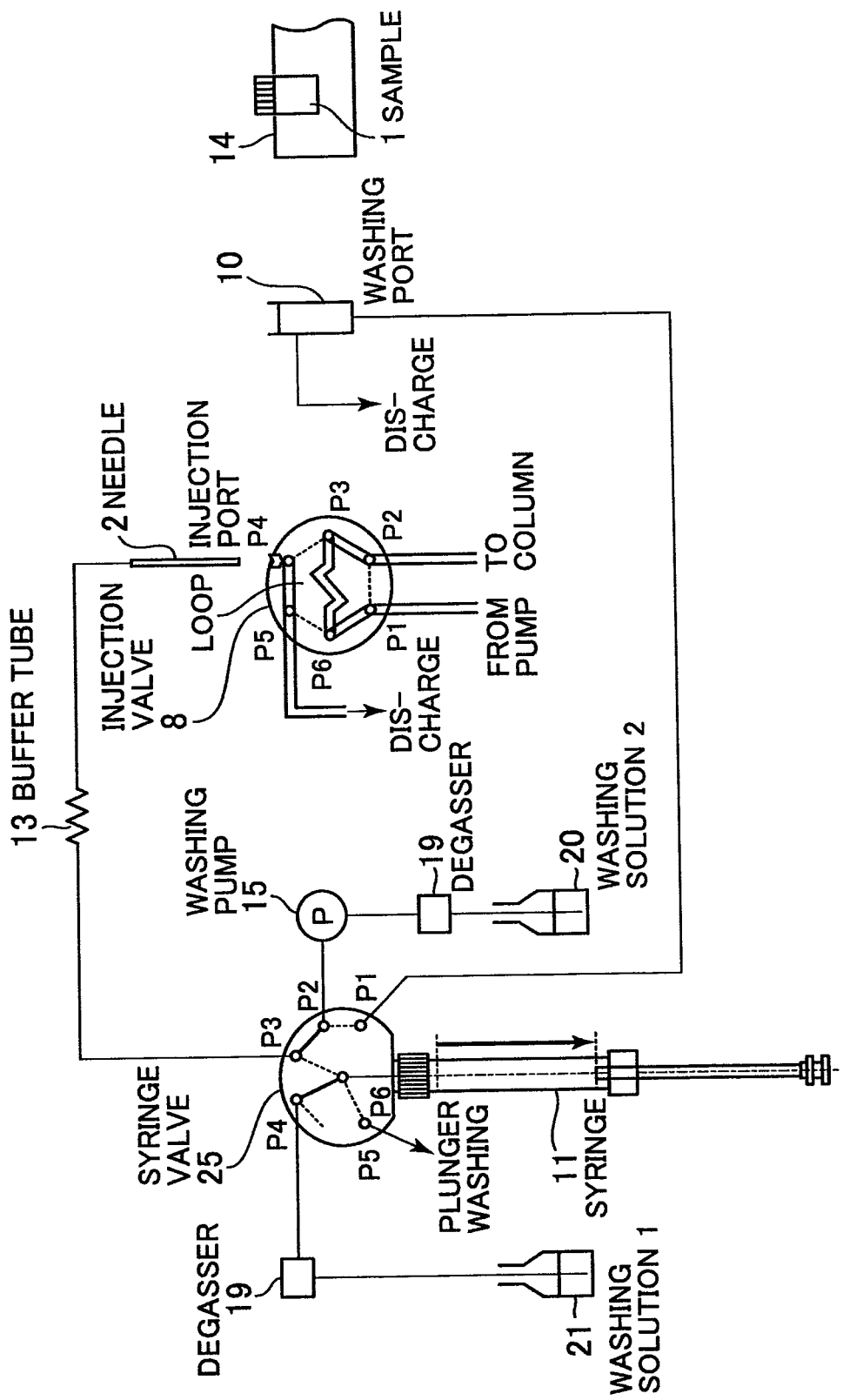
FIG. 39 is a drawing showing a schematic construction and a step for washing the plunger of the pump unit of a liquid chromatograph apparatus according to the fifth embodiment of the present invention.
Figure 40:
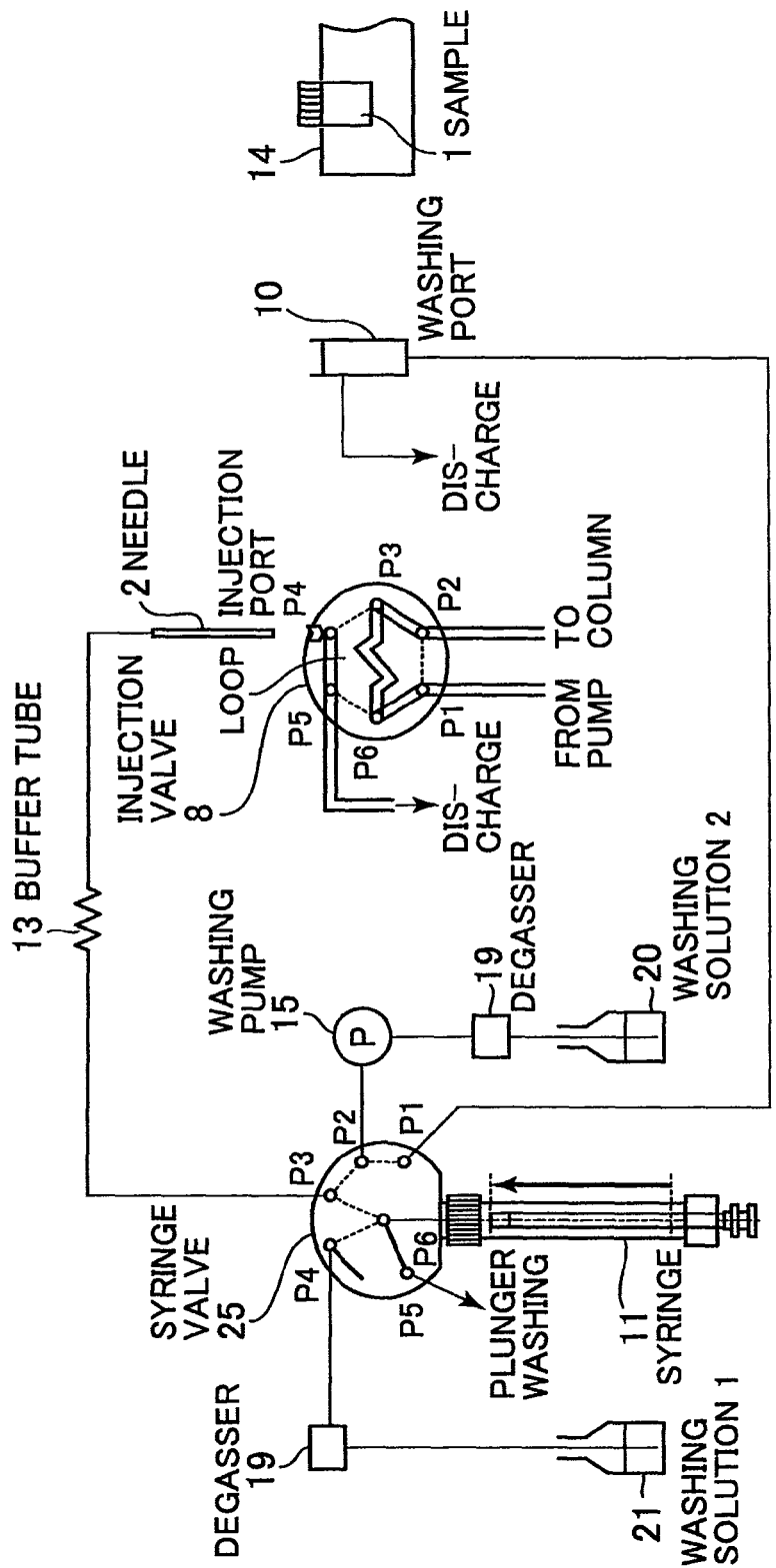
FIG. 40 is a drawing showing a schematic construction and a step for washing the plunger of the pump unit of a liquid chromatograph apparatus according to the fifth embodiment of the present invention.

FIGS. 39 and 40 are drawings to show the passage of the step for washing the plunger of the pump unit 7. In FIG. 39, the syringe 11 is moved downwardly to suck the washing solution B from the washing solution bottle 21. In FIG. 40, the 6-port 3-position valve 25 is rotated at 90 degrees in the counterclockwise to exchange the position into the position (3) to communicate the ports P5-P6. The syringe 11 is moved upwardly to wash the passages in the buffer pipe 13, the needle 2, the sample injection port 3, and the 6-port 2-position valve 8 by using the washing solution B, and the solution B is discharged to the plunger washing passage 17.

After the washing operation, the condition is shifted to the idling condition shown in FIG. 27.

Figure 41:
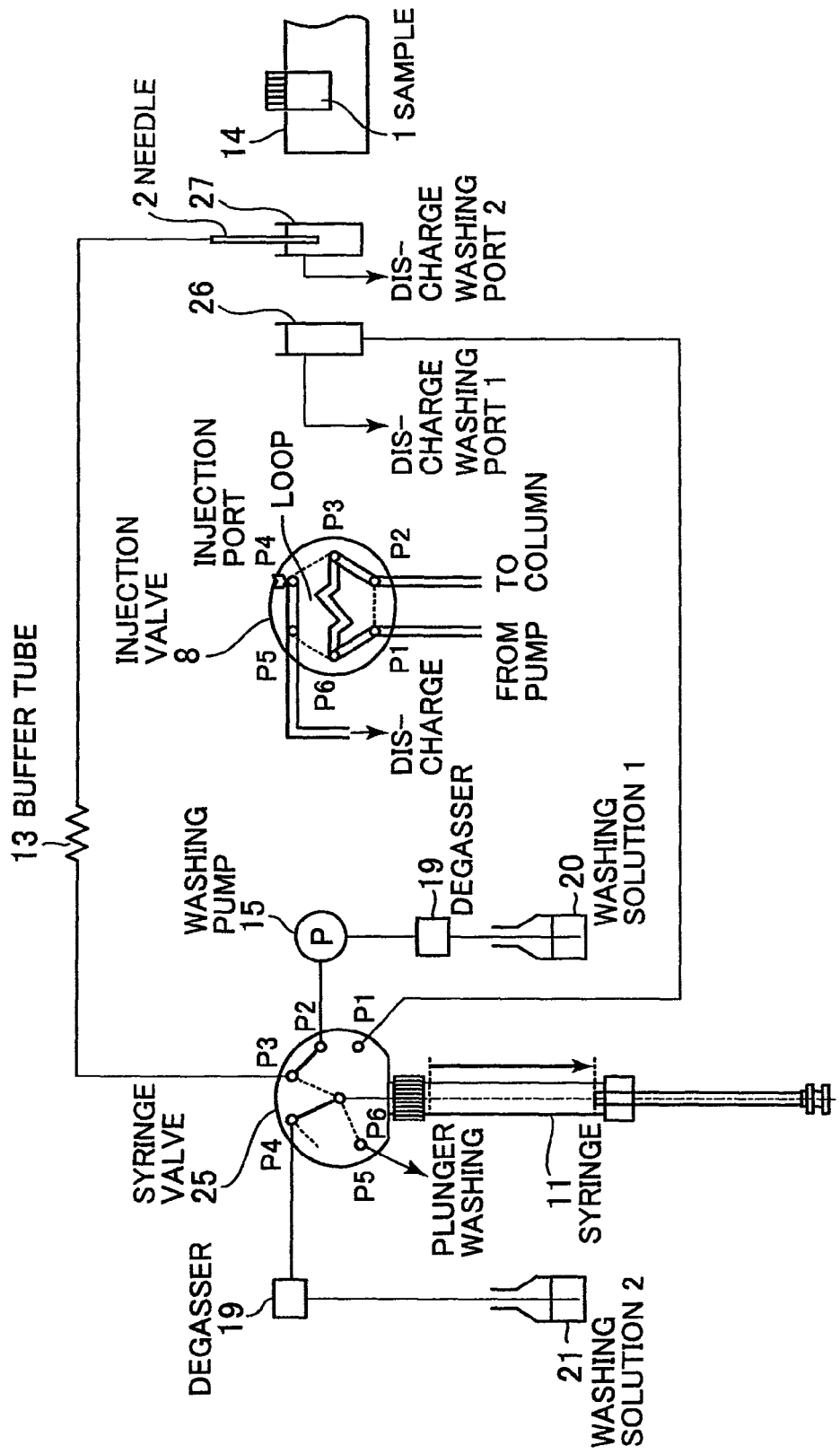
FIG. 41 is a drawing showing a schematic construction and a step for washing the external wall of the needle of a liquid chromatograph apparatus according to the fifth embodiment of the present invention.
Figure 42:
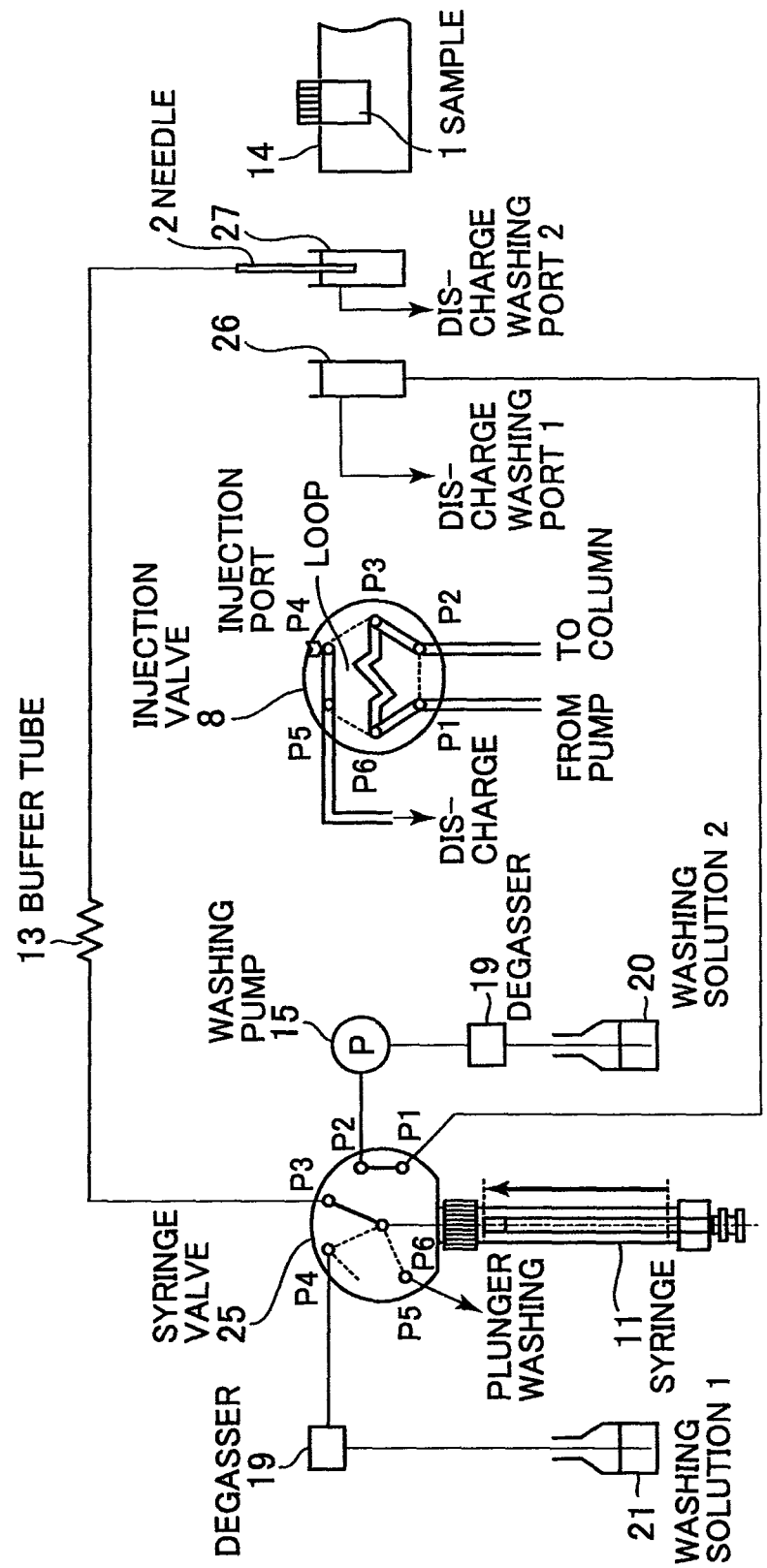
FIG. 42 is a drawing showing a schematic construction and a step for washing the external wall of the needle of a liquid chromatograph apparatus according to the fifth embodiment of the present invention.

FIGS. 41 and 42 are drawings to show the passage of the step for washing the external wall of the needle 2 by using the washing solution B in the washing solution bottle 21. In FIG. 41, the syringe 11 is moved downwardly to suck the washing solution B from the washing solution bottle 21.

In FIG. 42, the 6-port 3-position valve 25 is rotated at 45 degrees in the clockwise direction to exchange the position into the position (1) to communicate the ports P1-P2 and P3-P6 respectively. Further, after the needle 2 is moved to the washing tank 27, the syringe 11 is moved upwardly to discharge the washing tank B from the top end of the needle 2. After the external wall of the needle 2 is washed, the washing solution is discharged to the drain 28.

After the washing operation, the condition shifts the idling condition shown in FIG. 27.

Further, the same injection systems of the cut system of the first embodiment and the full loop system of the third embodiment can be realized by using the construction of the fifth embodiment.

The fifth embodiment of the present invention can also realize the liquid chromatograph apparatus and the automatic sample introducing apparatus used for the liquid chromatograph apparatus capable for improving the basic performance and for executing the processes at high speed and high reliability, as same as the first embodiment.

Figure 44:
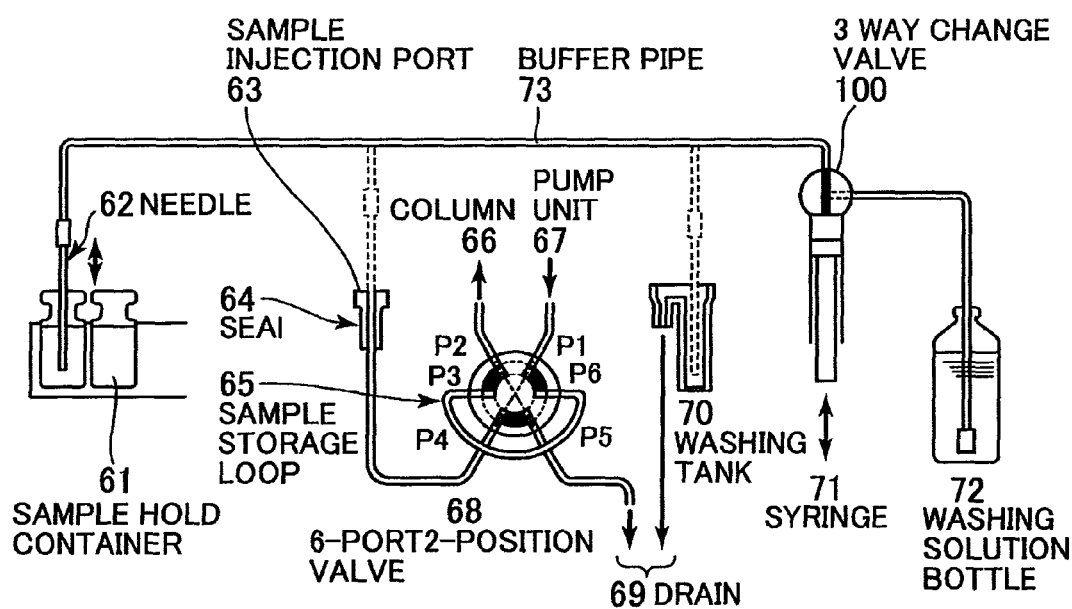
FIG. 44 shows an example of a sample introducing apparatus which is different from the present invention in order to compare with the present invention.

FIG. 44 is an example, which is different from the present invention, to execute both operations of sample accounting and the washing the passage by the syringe, the example shown in FIG. 44 is an example to compare with the present invention.

The example shown in FIG. 44 is one example of the automatic sample introducing apparatus of the loop injection system. In FIG. 44, the automatic sample introducing apparatus comprises a 6-port 2-position valve 68 used as a flow passage exchanging means, a needle 62, a syringe 71 used as a sample accounting means, a three way valve 100, and a washing solution bottle 72 mainly.

The 6-port 2-position valve 68 includes six ports of the port P1 connected to a sample introducing port 63, the port P2 for feeding the sample to a separation column 66, the port P1 for supplying the mobile phase fed from a pump unit 67, the ports P3 and P6 connected to the both ends of a sample storage loop 65, and the port P5 connected to a drain (discharge port) 69.

The sample injection operation is executed as follows; Firstly, the 6-port 2-position valve 68 is exchanged to the position shown by doted line, so that the sample injection port 63, the sample storage loop 65, and the drain 69 are communicated with each other. The needle 62 is inserted into the sample hold container 61 in condition that the three way valve 100 is connected to the syringe 71, and predetermined volume of the sample is sucked and held in the buffer pipe 73 by operating the syringe 71.

After the sample sucking operation, the needle 62 is dipped into the washing tank 70, and the sample attached on the external wall of the needle 62. After the washing operation, the needle 62 is moved into the sample introducing port 63, the sample being discharged into the sample introducing port 63 by operating the syringe 71. The sample discharged in the sample introducing port is stored in the sample storage loop 65 temporarily.

The position of the 6-port 2-position valve 68 is exchanged into the side shown by continuous line, so that the passage connecting the pump unit 67, the sample storage loop 65, and the column 66 is formed, and the analysis is started. The sample temporarily stored in the sample storage loop 65 is pushed with the mobile phase fed by the pump unit 67 into the column 66 to separate each of components.

After the each of the components separated with each other is detected by the detector as a chromatogram, each component is fed to the data processing unit to execute the qualification and quantitative process.

After the start of the analyzing operation, the inner wall, on which the sample is attached, of the needle 62 and the sample introducing port 63 are washed. The position of the three way valve 100 is exchanged into the position represented by a broken line, and the syringe 71 is operated, so that the washing solution is sucked from the washing solution bottle 72. Thereafter, the position of the three way valve 100 is again exchanged into the position represented by a continuous line, and the syringe 71 is operated, so that the washing solution is discharged into the buffer pipe 73, and the inner wall of the needle 62, sample introducing port 63, and the 6-port 2-position valve 68 are washed, and the washing solution is discharged to the drain 69.

According to the apparatus having the constructions as shown in FIG. 44, since the syringe executes for accenting the sample and for washing the flow passage, the frequency of the exchange of the syringe is extremely high. Further, if the syringe having small volume is used in order to be prior to the sample accounting, the washing time becomes long, and the cycle time becomes long. If the syringe having large volume is used in order to be prior to the flow passage washing, the accuracy and the resolution power of the syringe operation are deteriorated, as the result. Further, since the external wall of the needle can washed only by using an immersion washing, the sample attached on the external wall of the needle cannot be fully washed. It becomes a factor of a sample carryover.

On the other hand, the present invention can overcome the above-mentioned problem.

Further, the above-mentioned example is an application of the present invention applied to a liquid chromatograph apparatus. The present invention, however, can be applied to not only a liquid chromatograph apparatus but also other liquid sample analyzing apparatus. For, example, the present invention can be applied to an automatic analyzer, or an atomic absorption photometer.

DESCRIPTION OF REFERENCE NUMBERS

1 - - - sample hold container, 2 - - - needle, 3 - - - sample injection port, 5 - - - sample storage loop, 6 - - - separation column, 7 - - - pump unit, 8 - - - 6-port 2-position valve, 9 - - - drain, 10 - - - washing tank, 11 - - - syringe, 12 - - - washing solution bottle, 13 - - - buffer pipe, 14 - - - sample rack, 15 - - - washing unit, 16 - - - 5-port 4-position valve, 17 - - - pump plunger washing flow passage, 18 - - - three way valve, 19 - - - degassing unit, 20, 21 - - - washing solution bottle, 22, 23 - - - drain, 24 - - - pressure sensor, 6-port 3-position valve, 26, 27 - - - washing tank, 28 - - - drain, 30 - - - detector, 31 - - - washing solution pipe, 50 - - - control unit, 51 - - - needle moving mechanism, 52 - - - syringe moving mechanism, 53 - - - washing unit operation mechanism, 54 - - - syringe valve operation mechanism, 55 - - - three way valve operation mechanism, 56 - - - 2-position valve operation mechanism

The invention claimed is:

1. A liquid sample introducing apparatus having a mobile phase flow passage for introducing a sample into a liquid sample analyzing apparatus, comprising:
   a sample storage loop;
   a needle for sucking and discharging a sample;
   a first flow passage exchanging means having a sample injection port into which said needle is inserted, said first flow passage exchanging means exchanging whether separating said sample storage loop from said mobile phase flow passage and connecting said sample storage loop to said sample injection port or separating said sample storage loop from said sample injection port and connecting said sample storage loop to said mobile phase flow passage;
   a syringe means for accounting a sample and to suck a sample from a sample container into the needle and to discharge a sample into said sample storage loop from the needle;
   a washing tank into which said needle is inserted;
   a washing pump for feeding a washing solution;
   a second flow passage exchanging means for exchanging a connection and a separation of said needle with said syringe means, a connection and a separation of said needle and said washing pump, and a connection and a separation of said washing tank and said washing pump;
   a needle moving mechanism for moving said needle between an inner of said sample container, said sample injection port, and said washing tank; and
   a control unit for controlling operations of said first flow passage exchanging means, said syringe means, said washing pump, said second flow passage exchanging means, and said needle moving mechanism,
   wherein said second flow passage exchanging means connects said washing tank to and said washing pump in condition that said needle and said syringe means are connected with each other, and
   said washing pump feeds a washing solution to the inner of said needle and said washing tank through said second flow passage exchanging means.

2. A liquid sample introducing apparatus according to claim 1, further comprising a pressure sensor for detecting a feeding pressure from said washing pump.

3. A liquid sample analyzing apparatus having a mobile phase flow passage, comprising:
   a sample storage loop;
   a pump means for discharging a liquid sample from said sample storage loop;
   a needle for sucking and discharging a sample;
   a first flow passage exchanging means having a sample injection port into which said needle is inserted, said first flow passage exchanging means exchanging whether separating said sample storage loop from said mobile phase flow passage and connecting said sample storage loop to said sample injection port or separating said sample storage loop from said sample injection port and connecting said sample storage loop to said mobile phase flow passage;
   a syringe means for accounting a sample and to suck a sample from a sample container into the needle and to discharge a sample into said sample storage loop from the needle;
   a washing tank into which said needle is inserted;
   a washing pump for feeding a washing solution;
   a second flow passage exchanging means for exchanging a connection and a separation of said needle with said syringe means, a connection and a separation of said needle and said washing pump, and a connection and a separation of said washing tank and said washing pump;
   a needle moving mechanism for moving said needle between an inner of said sample container, said sample injection port, and said washing tank;
   a detection means for analyzing a liquid sample discharged from said sample storage loop;
   a control unit for controlling operations of said first flow passage exchanging means, said syringe means, said washing pump, said second flow passage exchanging means, said pump means and said needle moving mechanism,
   wherein said second flow passage exchanging means connects said washing tank to said washing pump in condition that said needle and said syringe means are connected with each other, and
   said washing pump feeds a washing solution to the inner of said needle and said washing tank through said second flow passage exchanging means.

4. A liquid sample analyzing apparatus according to claim 3, further comprising a pressure sensor for detecting a feeding pressure from said washing pump.

5. A liquid sample analyzing apparatus according to claim 4, further comprising a separation column connected between said first flow passage exchanging means and said detecting means, wherein said liquid sample analyzing apparatus is a liquid chromatograph apparatus.

6. A method for introducing a sample into a liquid sample analyzing apparatus having a mobile phase flow passage, comprising the steps of:
- a step for sucking a liquid sample into a needle which sucks and discharges a liquid sample while accounting a liquid sample by means of a syringe means;
- a step for connecting said needle to a sample injection port of a first flow passage exchanging means, and supplying a liquid sample sucked into said needle to a sample storage loop of said first flow passage exchanging means while accounting a liquid sample sucked in said needle by using said syringe means;
- a step for separating said needle from said sample injection port of said first flow passage exchanging means, and for supplying a liquid sample stored in said sample storage loop to said mobile phase flow passage;
- a step for connecting a washing tank with a washing pump, and said syringe means with said needle by a second flow passage exchanging means exchanging a connection and a separation of said needle with said syringe means, a connection and a separation of said needle and said washing pump, and a connection and a separation of said washing tank and said washing pump, and for feeding a washing solution by said washing pump to said washing tank to wash an external wall of a needle in condition that said external wall of said needle is inserted into said washing tank; and
- a step for separating said needle from said syringe means by said second flow passage exchanging means to connect said needle to said washing pump, and for supplying a washing solution into said needle by said washing pump, and for washing an inner wall of said needle.

7. A method for introducing a sample into a liquid sample analyzing apparatus according to claim 6, wherein a feeding pressure from said washing solution feeding means is detected by a pressure sensor for confirming a liquid feeding condition of a washing solution.

* * * * *